US012577300B2

(12) United States Patent
Cosgrove

(10) Patent No.: US 12,577,300 B2
(45) Date of Patent: Mar. 17, 2026

(54) NEUTRALIZING ANTIBODIES TO HUMAN ENDOTHELIN

(71) Applicant: Father Flanagan's Boys' Home Doing Business as Boys Town National Research Hospital, Omaha, NE (US)

(72) Inventor: Dominic Cosgrove, Omaha, NE (US)

(73) Assignee: Father Flanagan's Boys' Home Business, Omaha, NE (US)

( * ) Notice: Subject to any disclaimer, the term of this patent is extended or adjusted under 35 U.S.C. 154(b) by 1122 days.

(21) Appl. No.: 17/645,211

(22) Filed: Dec. 20, 2021

(65) Prior Publication Data

US 2022/0195034 A1 Jun. 23, 2022

Related U.S. Application Data

(63) Continuation of application No. PCT/US2020/038712, filed on Jun. 19, 2020.

(60) Provisional application No. 62/864,633, filed on Jun. 21, 2019.

(51) Int. Cl.
| | |
|---|---|
| *C07K 16/26* | (2006.01) |
| *A61K 39/395* | (2006.01) |
| *A61P 9/08* | (2006.01) |
| *A61P 13/12* | (2006.01) |
| *A61K 39/00* | (2006.01) |
| *C07K 14/575* | (2006.01) |
| *C12N 5/12* | (2006.01) |

(52) U.S. Cl.
CPC .......... *C07K 16/26* (2013.01); *A61K 39/3955* (2013.01); *A61P 9/08* (2018.01); *A61P 13/12* (2018.01); *A61K 2039/505* (2013.01); *C07K 14/57536* (2013.01); *C07K 2317/21* (2013.01); *C07K 2317/52* (2013.01); *C07K 2317/76* (2013.01); *C07K 2317/92* (2013.01); *C12N 5/12* (2013.01)

(58) Field of Classification Search
CPC .............. C07K 14/57536; C07K 16/26; A61K 39/3955; A61P 9/08; A61P 13/12
See application file for complete search history.

(56) References Cited

U.S. PATENT DOCUMENTS

| | | |
|---|---|---|
| 5,644,065 A | 7/1997 | Benoist et al. |
| 6,492,325 B1 | 12/2002 | Cosgrove |
| 7,348,002 B2 | 3/2008 | Cosgrove |
| 7,662,382 B2 | 2/2010 | Cosgrove |
| 2004/0186083 A1 | 9/2004 | McMahon et al. |
| 2011/0212083 A1 | 9/2011 | Reiser |
| 2011/0236397 A1 | 9/2011 | Reiser et al. |
| 2013/0216547 A1 | 8/2013 | Morton et al. |
| 2015/0175695 A1 | 6/2015 | Cosgrove |

FOREIGN PATENT DOCUMENTS

| | | |
|---|---|---|
| EP | 0331100 A1 | 9/1989 |
| EP | 0406628 B1 | 11/1994 |
| WO | 2014028059 A1 | 2/2014 |

OTHER PUBLICATIONS

Hocher et al., "Endothelial-1 Transgenic Mice Develop Glomerulosclerosis, Interstitial Fibrosis, and Renal Cysts but Not Hypertension", J Clin Invest., vol. 99, No. 6, pp. 1380-1389, 1997.
Horikoshi et al., "Abnormal Distribution of Mesangium-Specific Laminin in Glomeruli of Patients with Idiopathic Membranous Nephropathy", Nephron, vol. 81, No. 3, pp. 284-288, 1999.
Huang et al., "RhoB links PDGF signaling to cell migration by coordinating activation and localization of Cdc42 and Rac", J. Cell Biochem., vol. 112, No. 6, pp. 1572-1584, 2011.
International Searching Authority in connection with PCT/US2020/038712 filed Jun. 19, 2020, "Written Opinion of the International Searching Authority", 20 pages, mailed Oct. 16, 2020.
Jain et al., "Endothelin-1 Induces Endoplasmic Reticulum Stress by Activating the PLC-IP3 Pathway", The American Journal of Pathology, vol. 180, No. 6, pp. 2309-2320, Jun. 2012.
Just et al., "Dual constrictor and dilator actions of ETB receptors in the rat renal microcirculation: interactions with ETA receptors", Am J. Physiol Renal Physiol., vol. 286, pp. F660-F668, 2004.
Just et al., "NO and NO-independent mechanisms mediate ETB receptor buffering of ET-1-induced renal vasoconstriction in the rat", Am J Physiol Regul Integr Comp Physiol., vol. 288, No. 5, pp. R1168-R1177, 2005.
Kalluri et al., "Isoform Switching of Type IV Collagen is Developmentally Arrested In X-Linked Alport Syndrome Leading to Increased Susceptibility of Renal Basement Membranes to Endoproteolysis", J. Clin. Invest., vol. 99, No. 10, pp. 2470-2478, 1997.
Kalluri et al., "Assembly of Type IV Collagen," J Biol. Chem., vol. 275, No. 17, pp. 12719-12724, 2000.
Kamentetsky et al., "Analysis of the Glomerular Basement Membrane in Images of Renal Biopsies Using the Split-and-Merge Method: A Pilot Study", Journal of Digital Imaging, vol. 23, No. 4, pp. 463-474, 2010.
Kashtan et al., "Alport syndrome," Kidney Int., vol. 50, No. 5, pp. 1445-1463, 1996.
Kashtan et al., "Abnormal Glomerular Basement Membrane Laminins in Murine, Canine, and Human Alport Syndrome: Aberrant Laminin α2 Deposition Is Species Independent", J. Am. Soc. Nephrol., vol. 12, pp. 252-260, 2001.
Kashtan et al., "Chronology of renal scarring in males with Alport syndrome", Pediatric Nephrology, vol. 12, No. 4, pp. 269-274, 1998.
Kisanuki et al., "Low Blood Pressure in Endothelial Cell-Specific Endothelin 1 Knockout Mice", Hypertension, vol. 56, No. 1, pp. 121-128, 2010.

(Continued)

*Primary Examiner* — Zachary C Howard
(74) *Attorney, Agent, or Firm* — McKee, Voorhees & Sease, PLC

(57) ABSTRACT

This application provides antibodies and functional equivalents thereof which are capable of neutralizing endothelin-1, as well as their use in the treatment of disease conditions associated with endothelin-1 activation, such as Alport syndrome.

23 Claims, 17 Drawing Sheets
(2 of 17 Drawing Sheet(s) Filed in Color)
Specification includes a Sequence Listing.

(56)                    References Cited

OTHER PUBLICATIONS

Klabunde et al., "Endothelin", Cardiovascular Physiology, <URL:http://www.cvphysiology.com/Blood%20Flow/BF012.htm>; 2 pages, 2009.

Kleppel et al., "Evidence for Separate Networks of Classical and Novel Basement Membrane Collagen", J. Biol. Chem., vol. 267, No. 6, pp. 4137-4142, 1992.

Kodani et al., "GM130-dependent Control of Cdc42 Activity at the Golgi Regulates Centrosome Organization", Mol Biol Cell, vol. 20, No. 4, pp. 1192-1200, 2009.

Koepke et al., "Nephroprotective effect of the HMG-CoA-reductase inhibitor cerivastatin in a mouse model of progressive renal fibrosis in Alport syndrome", Nephrol Dial Transplant, vol. 22, pp. 1062-1069, 2007.

Kruegel et al., "Alport syndrome-insights from basic and clinical research", Nature Reviews Nephrology, vol. 9, pp. 170-178, 2013.

Kurihara et al., "Aortic Arch Malformations and Ventricular Septal Defect in Mice Deficient in Endothelin-1", J Clin Invest., vol. 96, No. 1, pp. 293-300, 1995.

Leivo et al., "Merosin, a protein specific for basement membranes of Schwann cells, striated muscle, and trophoblast, is expressed late in nerve and muscle development", Proc. Natl. Acad. Sci., vol. 85, pp. 1544-1548, Mar. 1988.

Li et al., "A Calcium-dependent Tyrosine Kinase Splice Variant in Human Monocytes", J Biol Chem., vol. 273, No. 16, pp. 9361-9364, 1998.

Ma et al., "Inhibition of Podocyte FAK Protects against Proteinuria and Foot Process Effacement", J Am Soc Nephrol., vol. 21, pp. 1145-1156, 2010.

Madrid et al., "The Formin INF2 Regulates Basolateral-to-Apical Transcytosis and Lumen Formation in Association with Cdc42 and MAL2", Dev Cell, vol. 18, No. 5, pp. 814-827, 2010.

Marsden et al., "Endothelial cell biology in relation to current concepts of vessel wall structure and function", J Am Soc Nephrol., vol. 1, No. 7, pp. 931-948, Jan. 1991.

Marsden et al., "Regulated expression of endothelin 1 in glomerular capillary endothelial cells", Am J Physiol., vol. 261, No. 1, pp. F117-F125, Jul. 1991.

Meehan et al., "Biomechanical strain causes maladaptive gene regulation, contributing to Alport glomerular disease", Kidney Int., vol. 76, pp. 968-976, 2009.

Meehan et al., "Endothelin-1 mediated induction of extracellular matrix genes in strial marginal cells underlies strial pathology in Alport mice", Hearing Research, vol. 341, pp. 100-108, 2016.

Miner et al., "The Laminin α Chains: Expression, Developmental Transitions, and Chromosomal Locations of α1-5, Identification of Heterotrimeric Laminins 8-11, and Cloning of a Novel α3 Isoform", J. Cell. Biol., vol. 137, No. 3, pp. 685-701, 1997.

Mochizuki et al., "Identification of mutations in the α3(IV) and α4(IV) collagen genes in autosomal recessive Alport syndrome", Nature Genesis, vol. 8,. pp. 77-82, 1994.

Nagase et al., "Substrate Specificity of MMPs", Cancer Drug Discovery and Development: Matrix Metalloproteinase Inhibitors in Cancer Therapy, pp. 39-66, 2001.

Neuhofer et al., "Role of endothelin and endothelin receptor antagonists in renal disease", European Journal of Clinical Investigation, vol. 36, Suppl. 3, pp. 78-88, 2006.

Nishiuchi et al., "Potentiation of the ligand-binding activity of integrin α1β1 via association with tetraspanin CD151", Proc Natl Acad Sci USA, vol. 102, No. 6, pp. 1939-1944, 2005.

Nobes et al., "Rho, Rae, and Cdc42 GTPases Regulate the Assembly of Multimolecular Focal Complexes Associated with Actin Stress Fibers, Lamellipodia, and Filopodia", Cell, vol. 81, pp. 53-62, 1995.

Oh et al., "Syndecan-1 enhances the endometrial cancer invasion by modulating matrix metalloproteinase-9 expression through nuclear factor κB", Gynecol Oneal., vol. 114, pp. 509-515, 2009.

Osmani et al., "Cdc42 localization and cell polarity depend on membrane traffic", J Cell Biol., vol. 191, No. 7, pp. 1261-1269, 2010.

Ostrow et al., "Stretch-Induced Endothelin-1 Production by Astrocytes", J Cardiovasc Pharmacol., vol. 36, Suppl. 1, pp. S274-S277, 2000.

Ostrow et al., "Stretch induced endothelin-1 secretion by adult rat astrocytes involves calcium influx via stretch-activated ion channels (SACs )", Biochem Biophys Res Commun., vol. 410, No. 1, pp. 81-86, 2011.

Parsons et al., "Focal adhesion kinase: the first ten years", J Cell Sci., vol. 116, No. 8, pp. 1409-1416, 2003.

Parsons et al., "Focal Adhesion Kinase: Targeting Adhesion Signaling Pathways for Therapeutic Intervention", Clinical Cancer Research, vol. 14, pp. 627-632, 2008.

Patton et al., "Distribution and Function of Laminins in the Neuromuscular System of Developing, Adult, and Mutant Mice", J. Cell Biol., vol. 139, pp. 1507-1521, 1997.

Pelish et al., "Secramine inhibits Cdc42-dependent functions in cells and Cdc42 activation in vitro", Nature Chemical Biology, vol. 2, pp. 39-46, 2006.

Person et al., "Modulation of Mesangial Cell Migration by Extracellular Matrix Components", Am J Pathol., vol. 133, No. 3, pp. 609-614, 1988.

Rao et al., "Role for Macrophage Metalloelastase in Glomerular Basement Membrane Damage Associated with Alport Syndrome", Am. J. Pathol., vol. 169, No. 1, pp. 32-46, 2006.

Ritz et al., "Endothelin Receptor Antagonists in Proteinuric Renal Disease: Every Rose Has Its Thorn", J Am. Soc. Nephrol., vol. 21, No. 3, pp. 392-394, 2010.

Rubin et al., "Bosentan Therapy for Pulmonary Arterial Hypertension", N Engl. J Med., vol. 346, No. 12, pp. 896-903, 2002.

Sachs et al., "Kidney failure in mice lacking the tetraspanin CD151", J Cell Biol., vol. 175, No. 1, pp. 33-39, 2006.

Sachs et al., "Blood pressure influences end-stage renal disease of Cd151 knockout mice", J Clin. Invest., vol. 122, No. 1, pp. 348-358, 2012.

Sampson et al., "Global Gene Expression Analysis Reveals a Role for the α1 Integrin in Renal Pathogenesis", J Biol Chem., vol. 276, No. 36, pp. 34182-34188, 2001.

Sanchez-Lopez et al., "Role of Zinc-binding- and Hemopexin Domain-encoded Sequences in the Substrate Specificity of Collagenase and Stromelysin-2 as Revealed by Chimeric Proteins", J Biol Chem., vol. 268, No. 10, pp. 7238-7247, 1993.

Abrahamson et al., "Laminin-1 reexpression in Alport mouse glomerular basement membranes," Kidney International, vol. 63, pp. 826-834, 2003.

Abrahamson et al., "Laminin Compensation in Collagen α3(IV) Knockout (Alport) Glomeruli Contributes to Permeability Defects", J. Am. Soc. Nephrol., vol. 18, pp. 2465-2472, 2007.

Abrahamson et al., "Steps on the Alport path to proteinuria", Kidney International, vol. 90, pp. 242-244, 2016.

Andrews et al., "Gelatinase B (MMP-9) Is Not Essential in the Normal Kidney and Does Not Influence Progression of Renal Disease in a Mouse Model of Alport Syndrome" Am. J. Pathol., vol. 157(1), pp. 303-311, 2000.

Aumailley et al., "A simplified laminin nomenclature", Matrix Biology, vol. 24, pp. 326-332, 2005.

Babu et al., "Mechanism of Stretch-Induced Activation of the Mechanotransducer Zyxin in Vascular Cells", Science Signaling, vol. 5, Issue 254, 11 pages, Dec. 11, 2012.

Baleato et al., "Deletion of Cd151 Results in a Strain-Dependent Glomerular Disease Due to Severe Alterations of the Glomerular Basement Membrane", Am. J. Pathol., vol. 173, No. 4, pp. 927-937, Oct. 2008.

Barker et al., "Identification of mutations in the COL4A5 collagen gene in Alport syndrome", Science, vol. 248, pp. 1224-1227, Jun. 1990.

Beg et al., "IκB interacts with the nuclear localization sequences of the subunits of NF-κB: a mechanism for cytoplasmic retention", Genes Dev., vol. 6, pp. 1899-1913, 1992.

Boffa et al., "Regression of renal vascular fibrosis by endothelin receptor antagonism", Hypertension, vol. 37(2), pp. 490-496. Feb. 2001.

Boor et al., "Treatment targets in renal fibrosis", Nephrol Dial Transplant, vol. 22, pp. 3391-3407, 2007.

Bossy et al., "Characterization of the integrin α8 subunit: a new integrin β1-associated subunit, which is prominently expressed on

(56) References Cited

OTHER PUBLICATIONS axons and on cells in contact with basal laminae in chick embryos", EMBO Journal, vol. 10, No. 9, pp. 2375-2385, 1991.

Bottero et al., "Monitoring NF-κB Transactivation Potential Via Real-Time PCR Quantification of IκB-α Gene Expression", Molecular Diagnosis, vol. 7(3-4), pp. 187-194, 2003.

Bursten et al., "Mesangial cell activation by bacterial endotoxin: Induction of rapid cytoskeletal reorganization and gene expression", American Journal of Pathology, vol. 139, No. 2, pp. 371-382, Aug. 1991.

Cattaruzza et al., "Shear Stress Insensitivity of Endothelial Nitric Oxide Synthase Expression as a Genetic Risk Factor for Coronary Heart Disease", Circulation Research, vol. 95, No. 8, pp. 841-847, 2004.

Chahdi et al., "The Rac/Cdc42 guanine nucleotide exchange factor β1Pix enhances mastoparan-activated Gi-dependent pathway in mast cells", Biochemical and Biophysical Research Communications, vol. 317, pp. 384-389, 2004.

Chahdi et al., "Endothelin 1 Induces β1Pix Translocation and Cdc42 Activation via Protein Kinase A-dependent Pathway", Journal of Biological Chemistry, vol. 280. No. 1, pp. 578-584, Oct. 28, 2004.

Chahdi et al., "Endothelin 1 stimulates β1 Pix-dependent activation of Cdc42 through the G(salpha) pathway", Experimental Biology and Medicine, vol. 231, No. 6, pp. 761-765, Jun. 2006.

Chen et al., "Osteopontin increases migration and MMP-9 up-regulation via αvβ3 integrin, FAK, ERK, and NF-κB-dependent pathway in human chondrosarcoma cells", Journal of Cellular Physiology, vol. 221, pp. 98-108, 2009.

Choe et al., "Wnt-Dependent Epithelial Transitions Drive Pharyngeal Pouch Formation", Developmental Cell, vol. 24, pp. 296-309, Feb. 11, 2013.

Cosgrove, Dominic, "Molecular Aspects of Alport Renal Disease Progression," Grant Abstract, Grant No. 5R01-DK055000-12. National Institutes of Health. Project dates Apr. 15, 1999 to Aug. 31, 2014 Retrieved from the Internet https://projectreporter.nih.gov/project_infodescription.cfm?aid=8534087&icde=31224167; 2 pgs, retrieved Sep. 23, 2016.

Cosgrove et al., "Collagen COL4A3 knockout: a mouse model for autosomal Alport syndrome", Genes & Development, vol. 10, pp. 2981-2992, 1996.

Cosgrove et al., "Integrin α1β1 and Transforming Growth Factor-β1 Play Distinct Roles in Alport Glomerular Pathogenesis and Serve as Dual Targets for Metabolic Therapy", American Journal of Pathology, vol. 157, No. 5, pp. 1649-1659, Nov. 2000.

Cosgrove, et al., "Integrin α1β1 Regulates Matrix Metalloproteinases via P38 Mitogen-Activated Protein Kinase in Mesangial Cells", The American Journal of Pathology, vol. 172, No. 3, pp. 761-773, Mar. 2008.

Cosgrove et al., "Collagen IV diseases: A focus on the glomeruiar basement membrane in Alport syndrome", Matrix Biol., pp. 1-10, 2016.

Crean et al., "Connective tissue growth factor [CTGF]/CCN2 stimulates mesangial cell migration through integrated dissolution of focal adhesion complexes and activation of cell polarization", The FASEB Journal, vol. 18, pp. 1541-1543, Oct. 2004.

Daniel et al., "Transgelin is a marker of repopulating mesangial cells after injury and promotes their proliferation and migration", Laboratory Investigation, vol. 92, pp. 812-826, 2012.

Deinhardt et al., "Neuronal Growth Cone Retraction Relies on Proneurotrophin Receptor Signaling Through Rac", Sci Signal., vol. 4, Issue 202, pp. 1-8, Dec. 2011.

Delimont et al., "Laminin α2-Mediated Focal Adhesion Kinase Activation Triggers Alport Glomerular Pathogenesis", PLOS ONE, vol. 9, Issue 6, e99083, pp. 1-14, 2014.

Dennis et al., "Collagen XIII Induced in Vascular Endothelium Mediates α1β1 Integrin-Dependent Transmigration of Monocytes in Renal Fibrosis", The American Journal of Pathology, vol. 177, No. 5, pp. 2527-2540, 2010.

Dufek et al., "Endothelin A receptor activation on mesangial cells initiates Alport glomerular disease", Kidney International, vol. 90, pp. 300-310, 2016.

Durvasula et al., "Mechanical strain increases SPARC levels in podocytes: implications for glomerulosclerosis", Am J Physiol Renal Physiol., vol. 289, pp. F577-F584, 2005.

Edlund et al., "Transforming Growth Factor-β-induced Mobilization of Actin Cytoskeleton Requires Signaling by Small GTPases Cdc42 and RhoA ", Molecular Biology of the Cell, vol. 13, pp. 902-914, Mar. 2002.

Ehrig et al., "Merosin, a tissue-specific basement membrane protein, is a laminin-like protein", Proc. Natl. Acad. Sci., vol. 87, pp. 3264-3268, May 1990.

Etienne-Manneville et al., "Integrin-Mediated Activation of Cdc42 Controls Cell Polarity in Migrating Astrocytes through PKCζ", Cell, vol. 106, pp. 489-498, Aug. 24, 2001.

Ferri et al., "Virtual Screening Approach for the Identification of New Rac1 Inhibitors", J. Med. Chem., vol. 52, pp. 4087-4090, 2009.

Fessler et al., "Lipid Rafts Regulate Lipopolysaccharide-induced Activation of Cdc42 and Inflammatory Functions of the Human Neutrophil", The Journal of Biological Chemistry, vol. 279, No. 38, Issue of Sep. 17, pp. 39989-39998, 2004.

Fischer et al., "Abnormal expression of glomerular basement membrane laminins in membranous glomerulonephritis", Nephrol Dial Transplant, vol. 15, pp. 1956-1964, 2000.

Frampton, James E., "Ambrisentan," Am J Cardiovasc Drugs, vol. 11, No. 4, pp. 215-226, 2011.

Gao et al., "Trp56 of Rac1 Specifies Interaction with a Subset of Guanine Nucleotide Exchange Factors", The Journal of Biological Chemistry, vol. 276, No. 50, Issue of Dec. 14, pp. 47530-47541, 2001.

Gao et al., "Rational design and characterization of a Rac GTPase-specific small molecule inhibitor", PNAS, vol. 101, No. 20, pp. 7618-7623, May 18, 2004.

Gardner et al., "Deletion of Integrin α1 by Homologous Recombination Permits Normal Murine Development but Gives Rise to a Specific Deficit in Cell Adhesion", Development Biology, vol. 175, Article No. 0116, pp. 301-313, 1996.

Gross et al., "Treatment of Alport syndrome: beyond animal models", Kidney International, vol. 76, pp. 599-603, 2009.

Gross et al., "Preemptive ramipril therapy delays renal failure and reduces renal fibrosis in COL4A3-knockout mice with Alport syndrome1", Kidney International, vol. 63, pp. 438-446, 2003.

Gunwar et al., "Glomerular Basement Membrane", The Journal of Biological Chemistry, vol. 273, No. 15, Issue of Apr. 10, pp. 8767-8775, 1998.

Hartner et al., "α8 Integrin in glomerular mesangial cells and in experimental glomerulonephritis", Kidney International, vol. 56, pp. 1468-1480, 1999.

Harvey et al., "Role of distinct type IV collagen networks in glomerular development and function", Kidney International, vol. 54, pp. 1857-1866, 1998.

Helbling-Leclerc et al., "Mutations in the laminin α2-chain gene (LAMA2) cause merosin-deficient congenital muscular dystrophy", Nat. Genet., vol. 11, pp. 216-218, 1995.

Hernández et al., "Novel Inhibitors of Rac1 in Metastatic Breast Cancer", Puerto Rico Health Sciences Journal, vol. 29, No. 4, pp. 348-356, Dec. 2010.

Hishikawa et al., "Pressure Enhances Endothelin-1 Release From Cultured Human Endothelial Cells", Hypertension, vol. 25, No. 3, pp. 449-452, 1995.

Sanlioglu et al., "Lipopolysaccharide Induces Rac1-dependent Reactive Oxygen Species Formation and Coordinates Tumor Necrosis Factor-α Secretion through IKK Regulation of NF-κB", J Biol Chem., vol. 276, No. 32, pp. 30188-30198, 2001.

Sayers et al., "Role for transforming growth factor-β1 in Alport renal disease progression", Kidney International, vol. 56, pp. 1662-1673, 1999.

Schlöndorff et al., "The Mesangial Cell Revisited: No Cell Is an Island", J Am Soc Nephrol., vol. 20, pp. 1179-1187, 2009.

Schnapp et al., "Sequence and tissue distribution of the human integrin α8 subunit: a β1-associated α subunit expressed in smooth muscle cells", J Cell Sci., vol. 108, pp. 537-544, 1995.

(56) References Cited

OTHER PUBLICATIONS

Shutes et al., "Specificity and Mechanism of Action of EHT 1864, a Novel Small Molecule Inhibitor of Rac Family Small GTPases", J Biol. Chem., vol. 282, pp. 32666-35678, 2007.

Simonson et al., "Endothelin-1 Stimulates Contraction of Rat Glomerular Mesangial Cells and Potentiates $\beta$-Adrenergic-mediated Cyclic Adenosine Monophosphate Accumulation", J Clin Invest., vol. 85, No. 3, pp. 790-797, 1990.

Sorokin, Andrey, "Endothelin signaling and actions in the renal mesangium", Contrib. Nephrol., vol. 172, pp. 50-62, 2011.

St. John et al., "Glomerular endothelial cells and podocytes jointly synthesize laminin-1 and -11 chains", Kidney International, vol. 60, pp. 1037-1046, 2001.

Surviladze et al., "A Potent and Selective Inhibitor of Cdc42 GTPase", Molecular Libraries Pathways to Discovery, Probe Report, pp. 1-27, 2010.

Takeda et al., "Deletion of tetraspanin Cd151 results in decreased pathologic angiogenesis in vivo and in vitro", Blood, vol. 109, No. 4, pp. 1524-1532, 2007.

Tracleer Bonsentan Tablets Datasheet, Actelion Pharmaceuticals US, pp. 1-6, 2012.

Tseng et al., "FAK activation is required for TNF-$\alpha$-induced IL-6 production in myoblasts", J Cell Physiol., vol. 223, pp. 389-396, 2010.

Van Slambrouck et al., "Activation of the FAK-src molecular scaffolds and p130Cas-JNK signaling cascades by $\alpha$1-integrins during colon cancer cell invasion", Int J Oncol., vol. 31, pp. 1501-1508, 2007.

Vatter et al., "Ambrisentan, a Non-peptide Endothelin Receptor Antagonist", Cardiovascular Drug Reviews, vol. 24, No. 1, pp. 63-76, 2006.

Vincente-Manzanares et al., "Integrins in cell migration-the actin connection", J Cell Sci., vol. 122, pp. 199-206, 2009.

Wendel et al., "Distribution of Endothelin Receptor Subtypes ETA and ETB in the Rat Kidney", J Histochem Cytochem., vol. 54, No. 11, pp. 1193-1203, 2006.

Wójtowicz et al., "Zyxin Mediation of Stretch-Induced Gene Expression in Human Endothelial Cells", Circ Res., vol. 107, No. 7, pp. 898-902, 2010.

Wyss et al., "Biophysical properties of normal and diseased renal glomeruli", Am. J. Physiol. Cell Physiol., vol. 300, pp. C397-C405, 2011.

Yamamoto et al., "Endothelin B Receptor-like Immunoreactivity in Podocytes of the Rat Kidney", Arch Histol Cytol., vol. 65, No. 3, pp. 245-250, 2002.

Yeh et al., "The antioxidative effect of bone morphogenetic protein-7 against high glucose-induced oxidative stress in mesangial cells", Biochem Biophys Res Commun., vol. 382, No. 2, pp. 292-297, 2009.

Zallocchi et al., "$\alpha$1$\beta$1 Integrin/Rac I-Dependent Mesangial Invasion of Glomerular Capillaries in Alport Syndrome", Am. J. Pathol., vol. 183, No. 4, pp. 1269-1280, 2013.

Zamudio-Meza et al., "Cross-talk between Rac1 and Cdc42 GTPases regulates formation of filopodia required for dengue virus type-2 entry into HMEC-1 cells", J Gen Virol., vol. 90, pp. 2902-2911, 2009.

Zeisberg et al., "Stage-Specific Action of Matrix Metalloproteinases Influences Progressive Hereditary Kidney Disease", PLOS Medicine, vol. 3, No. 4, e100, pp. 535-546, 2006.

Zeng et al., "Role of Focal Adhesion Kinase and Phosphatidylinositol 3'-Kinase in Integrin Fibronectin Receptor-Mediated, Matrix Metalloproeinase-1-Dependent Invasion by Metastatic Prostate Cancer Cells", Cancer Res., vol. 66, No. 16, pp. 8091-8099, 2006.

Nishida et al., "Endothelin-1, an ulcer inducer, promotes gastric ulcer healing via mobilizing gastric myofibroblasts and stimulates production of stroma-derived factors", Am. J Physiol Gastrointest Liver Physiol., vol. 290, pp. G1041-G1050, 2006.

Licht et al., "ETB-Receptor Blockade Reduces Tubulointerstitial Fibrosis Caused by Chronic Proteinuria in COL4A3 Knockout Mice", Poster No. TH-PO471, J Am Soc Nephrol., vol. 16, 1 page, 2005.

Vincente-Manzanares et al., "Integrins in cell migration—the actine connection", Author Correction, J. Cell. Sci.., vol. 122, p. 1473, 2009.

FIG. 2

Section

Nab #7 ET-1

CD31

Dual

Injected Nab #7

Real Time Gene Expression

| | %SG | FS | Albumin | BUN | Glomeruli RNA MMP-9 | MMP-10 | MMP-12 | MCP-1 | IL6 | Cortex RNA MCP-2 | MMP-9 | TNF-α | Life Span |
|---|---|---|---|---|---|---|---|---|---|---|---|---|---|
| Average | 43% | 2.5 | 26.3 | 24.3 | 5.33 | 4600.26 | 12.12 | 141.14 | 4.01 | 11.84 | 21.90 | 40.84 | 11.2 |
| STD DEV | 2% | 1.1 | 14.3 | 6.1 | 1.39 | 2196.07 | 7.48 | 93.23 | 1.89 | 6.04 | 12.75 | 27.83 | 1.2 |
| n | 30 | 29 | 28 | 15 | 6 | 5 | 6 | 6 | 6 | 7 | 7 | 7 | 21 |
| k | 1 | 1 | 1 | 1 | 1 | 1 | 1 | 1 | 1 | 1 | 1 | 1 | 1 |
| α Error | 0.05 | 0.05 | 0.05 | 0.05 | 0.05 | 0.05 | 0.05 | 0.05 | 0.05 | 0.05 | 0.05 | 0.05 | 0.05 |
| β Error | 0.2 | 0.2 | 0.2 | 0.2 | 0.2 | 0.2 | 0.2 | 0.2 | 0.2 | 0.2 | 0.2 | 0.2 | 0.2 |
| Power | 80% | 80% | 80% | 80% | 80% | 80% | 80% | 80% | 80% | 80% | 80% | 80% | 80% |

Minimum Sample Size Required Per Group for Sufficient Statistical Power

| Anticipated % Difference of Treated Group Compared to Untreated | | | | | | | | | | | | | | |
|---|---|---|---|---|---|---|---|---|---|---|---|---|---|---|
| 25% Decrease | 63 | 17 | 49 | 74 | 16 | 17 | 57 | 96 | 110 | 56 | 65 | 85 | 117 | 2 WK Increase   6 |
| 50% Decrease | 17 | 12 | 19 | 4 | 4 | 14 | 24 | 27 | 14 | 16 | 21 | 29 | | 4 WK Increase   1 |
| 75% Decrease | 7 | 5 | 8 | 2 | ▨ | 6 | 11 | 12 | 6 | 7 | 9 | 13 | | 6 WK Increase   1 |

Calculations: k = 1

$$n = \frac{(2*\sigma^2/k)(Z_{1-\alpha/2}+Z_{1-\beta})^2}{\Delta^2}$$

Key:
$\Delta = |\mu_2 - \mu_1|$ = Absolute Difference Between Two Means
$\sigma$ = Standard DEV for Untreated and Treated Group (Assuming the Same)
$n$ = Sample Size for Untreated and Treated Group (Assuming the Same)
$\alpha$ = Probability of Type I Error (Usually 0.05) - False Positive Rate
$\beta$ = Probability of Type II Error (Usually 0.02) - False Negative Rate
$z$ = Critial Z Value for a Given $\alpha$ or $\beta$
$k$ = Ratio of Sample Size for Treated Group to Untreated Group

FIG. 16

Real Time Gene Expression: Glomeruli

|  | %SG | FS | BUN | MMP-2 | MMP-9 | MMP-10 | MMP-12 | MMP-14 | Life Span |
|---|---|---|---|---|---|---|---|---|---|
| Average | 73% | 5.0 | 67.24 | 2.66 | 0.50 | 2924.21 | 9.59 | 0.79 | 27.8 |
| STD DEV | 14% | 0.0 | 14.90 | 2.51 | 0.28 | 1807.76 | 4.08 | 0.44 | 0.9 |
| n | 10 | 9 | 5 | 8 | 8 | 8 | 8 | 8 | 3 |
| Ratio of Sample Size | 1 | 1 | 1 | 1 | 1 | 1 | 1 | 1 | 1 |
| Alpha Error (False Positive Rate) | 0.05 | 0.05 | 0.05 | 0.05 | 0.05 | 0.05 | 0.05 | 0.05 | 0.05 |
| Beta Error (False Negative Rate) | 0.2 | 0.2 | 0.2 | 0.2 | 0.2 | 0.2 | 0.2 | 0.2 | 0.2 |
| Power | 80% | 80% | 80% | 80% | 80% | 80% | 80% | 80% | 80% |

Minimum Sample Size Required Per Group for Sufficient Statistical Power

| Anticipated % Difference of Treated Group Compared to Untreated | %SG | FS | BUN | MMP-2 | MMP-9 | MMP-10 | MMP-12 | MMP-14 | Life Span |
|---|---|---|---|---|---|---|---|---|---|
| 25% Decrease | 9 | 0 | 12 | 224 | 85 | 96 | 45 | 78 | 5 WK Increase: 1 |
| 50% Decrease | 2 | 0 | 3 | 56 | 20 | 24 | 11 | 19 | 10 WK Increase: 1 |
| 75% Decrease | 1 | 0 | 1 | 25 | 9 | 11 | 5 | 9 | 15 WK Increase: 1 |

Key: $\Delta = |\mu_2 - \mu_1|$ = Absolute Difference Between Two Means
$\sigma_1, \sigma_2$ = Standard DEV of Group #1 and #2 (Assuming the Same)
$n_1$ = Sample Size for for Group #1
$n_2$ = Sample Size for for Group #2
$\alpha$ = Probability of Type I Error (Usually 0.05)
$\beta$ = Probability of Type II Error (Usually 0.02)
$z$ = Critial Z Value for a Given $\alpha$ or $\beta$
$k$ = Ratio of Sample Size for Group #2 to Group #1

Calculations: $k = \dfrac{n_2}{n_1} = 1$ $$n_1 = n_2 = \frac{(\sigma_1^2 + \sigma_2^2/k)(Z_{1-\alpha/2} + Z_{1-\beta})^2}{\Delta^2}$$

FIG. 17

SEQUENCE LISTING

```
<160> NUMBER OF SEQ ID NOS: 1

<210> SEQ ID NO 1
<211> LENGTH: 21
<212> TYPE: PRT
<213> ORGANISM: Homo sapiens

<400> SEQUENCE: 1

Cys Ser Cys Ser Ser Leu Met Asp Lys Glu Cys Val Tyr Phe Cys His
1               5                   10                  15

Leu Asp Ile Ile Trp
            20
```

NEUTRALIZING ANTIBODIES TO HUMAN ENDOTHELIN

This application is a By-Pass Continuation claiming priority to PCT/US2020/038712, filed Jun. 19, 2020, which application claims the benefit of U.S. Provisional Application Ser. No. 62/864,633, filed Jun. 21, 2019, which are incorporated by reference herein.

REFERENCE TO SEQUENCE LISTING SUBMITTED ELECTRONICALLY

The instant application contains a Sequence Listing which has been submitted electronically in ASCII plain text format and is herein incorporated by reference in its entirety. Said TXT copy, created on Jun. 7, 2025, is named "P13504US01 SequenceListing.txt" and is 651 bytes in size.

BACKGROUND

Alport syndrome is a genetic disorder characterized by abnormalities in the basement membranes of the glomerulus (leading to hematuria, glomerulosclerosis, and end-stage kidney disease (ESRD)), cochlea (causing deafness), and eye (resulting in lenticonus and perimacular flecks). Alport syndrome is a primary basement membrane disorder caused by mutations in the collagen type IV COL4A3, COL4A4, or COL4A5 genes. Mutations in any of these genes prevent the proper production or assembly of the type IV collagen network, which is an important structural component of basement membranes in the kidney, inner ear, and eye. Basement membranes are thin, sheet-like structures that separate and support cells in many tissues. The abnormalities of type IV collagen in kidney glomerular basement membranes leads to irregular thickening and thinning and splitting of these basement membranes, causing gradual scarring (fibrosis) of the kidneys. Alport Syndrome has a delayed onset and causes progressive kidney damage. The glomeruli and other normal kidney structures such as tubules are gradually replaced by scar tissue, leading to kidney failure. Hearing loss and an abnormality in the shape of the lens called anterior lenticonus are other important features of Alport Syndrome. People with anterior lenticonus may have problems with their vision and may develop cataracts. The prevalence of Alport syndrome is estimated at approximately 1 in 5,000 births and it is estimated that the syndrome accounts for approximately 2.1 percent of pediatric patients with ESRD. Currently there is no specific treatment for Alport Syndrome; treatments are symptomatic. Patients are advised on how to manage the complications of kidney failure and the proteinuria that develops is often treated with ACE inhibitors. Once kidney failure has developed, patients are given dialysis or can benefit from a kidney transplant, although this can cause problems. The body may reject the new kidney as it contains normal type IV collagen, which may be recognized as foreign by the immune system. Thus, there is a need for improved therapeutic agents for the treatment of Alport syndrome.

SUMMARY OF THE INVENTION

The present invention includes an antibody or antigen binding fragment thereof capable of specifically binding human endothelin-1, the antibody or antigen binding fragment thereof comprising a heavy chain complementarity determining region (CDR) 1, a heavy chain variable region CDR2, a heavy chain variable region CDR3, a light chain variable region CDR1, a light chain variable region CDR2, and a light chain variable region CDR3 of the monoclonal antibody produced by the hybridoma cell line Nab #15 7D 489 deposited under ATCC[[®]] Patent Deposit Designation PTA-125817.

The present invention includes an antibody or antigen binding fragment thereof capable of specifically binding human endothelin-1, the antibody or antigen binding fragment thereof comprising a heavy chain complementarity determining region (CDR) 1, a heavy chain variable region CDR2, a heavy chain variable region CDR3, a light chain variable region CDR1, a light chain variable region CDR2, and a light chain variable region CDR3 of the monoclonal antibody produced by the hybridoma cell line Nab #7 3G 9A4 deposited under ATCC[[®]] Patent Deposit Designation PTA-125818.

The present invention includes an antibody or antigen binding fragment thereof capable of specifically binding human endothelin-1, the antibody or antigen binding fragment thereof comprising a heavy chain complementarity determining region (CDR) 1, a heavy chain variable region CDR2, a heavy chain variable region CDR3, a light chain variable region CDR1, a light chain variable region CDR2, and a light chain variable region CDR3 of the monoclonal antibody produced by the hybridoma cell line Nab #1 5D 1087 deposited under ATCC[[®]] Patent Deposit Designation PTA-125819.

The present invention includes an antibody or antigen binding fragment thereof capable of specifically binding human endothelin-1, the antibody or antigen binding fragment thereof comprising the heavy chain variable region (VH) and light chain variable region (VL) of the monoclonal antibody produced by the hybridoma cell line Nab #15 7D 489 deposited under ATCC[[®]] Patent Deposit Designation PTA-125817.

The present invention includes an antibody or antigen binding fragment thereof capable of specifically binding human endothelin-1, the antibody or antigen binding fragment thereof comprising the heavy chain variable region (VH) and light chain variable region (VL) of the monoclonal antibody produced by the hybridoma cell line Nab #7 3G 9A4 deposited under ATCC[[®]] Patent Deposit Designation PTA-125818.

The present invention includes an antibody or antigen binding fragment thereof capable of specifically binding human endothelin-1, the antibody or antigen binding fragment thereof comprising the heavy chain variable region (VH) and light chain variable region (VL) of the monoclonal antibody produced by the hybridoma cell line Nab #1 5D 1087 deposited under ATCC[[®]] Patent Deposit Designation PTA-125819.

In some aspects, the antigen binding fragment thereof is selected from the group consisting of a Fab fragment, a Fab' fragment, a F(ab)2 fragment, a Fv fragment, and a single chain variable fragment (scFv).

In some aspects, the antibody or a functional part thereof is fully human, humanized, or chimeric.

In some aspects, the antibody or antigen binding fragment thereof comprises a human IgG1 isotype.

In some aspects, the antibody or antigen binding fragment thereof of comprises an Fc region comprising tyrosine (Y) at amino acid position 252, threonine (T) at amino acid position 254, and glutamic acid (E) at amino acid position 256, wherein the numbering corresponds to the EU index in Kabat.

The present invention includes the monoclonal antibody produced by hybridoma cell line Nab #15 7D 489 deposited under ATCC[[®]] Patent Deposit Designation PTA-125817, or an antigen binding fragment thereof.

The present invention includes the monoclonal antibody produced by hybridoma cell line Nab #7 3G 9A4 deposited under ATCC[[®]] Patent Deposit Designation PTA-125818, or an antigen binding fragment thereof.

The present invention includes the monoclonal antibody produced by hybridoma cell line Nab #1 5D 1087 deposited under ATCC[[®]] Patent Deposit Designation PTA-125819, or an antigen binding fragment thereof.

In some aspects, the antibody or antigen binding fragment thereof neutralizes the activity of human endothelin-1.

In some aspects, the antibody or antigen binding fragment thereof inhibits the formation of drebrin-positive filopodial microspikes in cultured mesangial cells contacted with endothelin-1.

In some aspects, the antibody or antigen binding fragment thereof inhibits the polymerization of globular actin (G-actin) to filamentous actin (F-actin) in cultured mesangial cells contacted with endothelin-1.

The present invention includes compositions comprising an antibody or antigen binding fragment thereof of as described herein.

The present invention includes kits comprising a monoclonal antibody or antigen binding fragment thereof as described herein.

The present invention includes the Nab #15 7D 489 hybridoma cell line as deposited under ATCC[[®]] Patent Deposit Designation PTA-125817, and progeny thereof.

The present invention includes the Nab #7 3G 9A4 hybridoma cell line as deposited under ATCC[[®]] Patent Deposit Designation PTA-125818, and progeny thereof.

The present invention includes the Nab #1 5D 1087 hybridoma cell line as deposited under ATCC[[®]] Patent Deposit Designation PTA-125819, and progeny thereof.

The present invention includes a method of treating Alport syndrome in a subject, the method comprising administering an effective amount of an antibody or antigen binding fragment thereof as described herein to the subject.

The present invention includes a method of preventing glomerular disease progression in a subject diagnosed with Alport syndrome, the method comprising administering an effective amount of an antibody or antigen binding fragment as described herein to the subject.

The present invention includes a method of treating glomerulonephritis in a subject, the method comprising administering an effective amount of an antibody or antigen binding fragment thereof as described herein to the subject.

The present invention includes a method of treating kidney injury due to biomechanical strain in Alport syndrome, the method comprising administering an effective amount of an antibody or antigen binding fragment part thereof as described herein to the subject.

The present invention includes a method of inhibiting deposition of laminin 211 in the glomerular basement membrane (GBM) in a subject, the method comprising administering an effective amount of an antibody or antigen binding fragment thereof of as described herein to the subject.

The present invention includes a method of inhibiting mesangial cell process invasion of the glomerular capillary loop in a kidney of a subject, the method comprising administering an effective amount of an antibody or antigen binding fragment thereof of as described herein to the subject.

The present invention includes a method of inhibiting Alport glomerular pathogenesis in a subject; the method comprising: determining that the subject is at risk for developing Alport glomerular disease; and administering an effective amount of an antibody or antigen binding fragment thereof of as described herein to the subject. In some aspects, the determination that the subject is at risk for developing Alport glomerular disease is determined by family medical history, genetic testing, immunodiagnostic skin biopsy testing, and/or molecular diagnostic marker testing.

In some aspects, with the methods described herein one or more sensory and/or hearing losses associated with Alport syndrome is treated or prevented.

The present invention includes a method of treating pulmonary hypertension in a subject, the method comprising administering an effective amount of an antibody or antigen binding fragment thereof of as described herein to the subject.

The present invention includes a method of treating diabetic kidney nephropathy in a subject, the method comprising administering an effective amount of an antibody or antigen binding fragment thereof of as described herein to the subject.

The present invention includes a method of inhibiting endothelin-1 induced pathogenesis in a subject, the method comprising administering an effective amount of an antibody or antigen binding fragment thereof of as described herein to the subject.

In some aspects, any of the methods described herein further comprise administering an angiotensin-converting enzyme (ACE) inhibitor. In some aspects, the ACE inhibitor is selected from ramipril and/or analapril.

In some aspects, any of the methods described herein further comprise administering an endothelin receptor antagonist. In some aspects, the endothelin receptor antagonist is selected from bosentan, sitaxsentan, ambrisentan, macitentan, sparsentan, and/or altrasentan.

The present invention includes an isolated nucleic acid sequence encoding the antibody or antigen binding fragment thereof of as described herein.

The present invention includes an isolated polynucleotide sequence comprising the nucleic acid sequence coding for the heavy chain, the light chain, the heavy chain variable region, the light chain variable region, or one or more complementarity determining regions of the antibody or antigen binding fragment thereof of as described herein.

The present invention includes an expression vector comprising an isolated polynucleotide as described herein.

The present invention includes a host cell comprising an expression vector as described herein.

The present invention includes a method of producing a substantially purified antibody, or antigen binding fragment thereof, the method comprising growing a host cell as described herein under conditions in which the antibody, or antigen binding fragment thereof, is expressed and harvesting the expressed antibody, or antigen binding fragment thereof.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also, herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

BRIEF DESCRIPTION OF THE FIGURES

The patent or application file contains at least one drawing executed in color. Copies of this patent or patent application publication with color drawings will be provided by the Office upon request and payment of the necessary fee.

FIG. 2. Glomerular RNA from Alport mice treated with vehicle, Sitaxentan, or nAb #7 was analyzed using QIAGEN mouse fibrosis microarray. The data reveal that Sitaxentan (and Ambrisentan) induce a number of pro-fibrotic genes, including Snail1, which is known to play a key role in promoting renal fibrosis (Grande et al., 2015, *Nat Med;* 21(9):989-97). Treatment with nAb #7 or vehicle does not induce these genes. The data is consistent with aberrant signaling activation by classic small molecule ETAR antagonists that results in pro-fibrotic effects, defining a clear potential advantage of the biologic over small molecule approach.

In FIG. 3A, dual staining demonstrates absence of integrin α8 immunostaining in the glomerular capillaries, which are dual stained with either anti-laminin α2 (upper panels) or anti-laminin α5 (lower panels) antibodies. Arrows denote integrin α8 immunopositivity in the capillary loops of the glomeruli from untreated Alport mice, and the relative absence of integrin α8 immunopositivity in the Sitaxentan-treated mice. With FIG. 3B, TEM analysis shows Sitaxentan ameliorates GBM dysmorphology largely normalizing the irregular thickening and thinning observed for the GBM of 7-week-old Alport mice.

In FIG. 4A, urine was collected at the indicated timepoints and analyzed for albumin using an ELISA kit. Albumin measures were normalized to urinary creatinine. Note that measurable albumin in the Sitaxentan-treated mice was not detected until 6 weeks of age, consistent with a delayed onset of glomerular disease. In FIG. 4B, BUN measures were performed on serum from 7-week-old vehicle or Sitaxentan-treated Alport mice.

In FIG. 5A, interstitial fibrosis was scored (blinded) for slides dual stained for fibronectin and anti-CD45 (pan leukocyte antigen. In FIG. 5B, sclerotic glomeruli were counted (blindly) and plotted as percent relative to the total number of glomeruli (five animals per group). In FIG. 5C, Sitaxentan treatment reduces mRNA expression of MMP-9, MMP-10, MMP-12, MCP-1, and IL-6 in glomeruli from Alport mice. Glomerular RNA from Sitaxentan-treated and vehicle-treated mice was analyzed by real time RT-PCR for the indicated transcripts. MMP, matrix metalloproteinase; MCP-1, monocyte chemoattractant protein-1; IL-6, interleukin 6. *P<0.001.

FIG. 9A shows Ab7 labeling of the glomerular endothelium. FIG. 9B shows labeling with antiCD31 antibodies (a marker for endothelial cells). The dual staining shown in FIG. 9C demonstrates that the anti-endothelin antibodies localize to the glomerular endothelium, consistent with earlier work (Dufek et al., 2016, *Kidney Int;* 90(2):300-310).

Figure 10B:
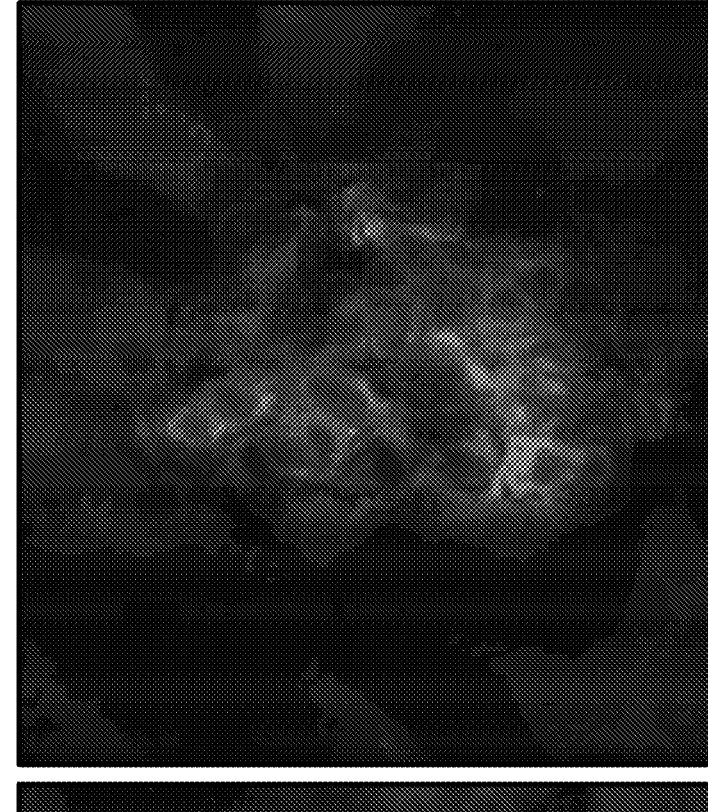
FIGS. 10A and 10B. Subcutaneously injected nAb #7 targets the glomerular endothelium: nAb #7 was fluorescently labeled. Twenty micrograms of the antibody was injected subcutaneously in a 6-week-old 129 Sv wild type mouse. Two hours later the animal was perfused transcar-
Figure 10A:
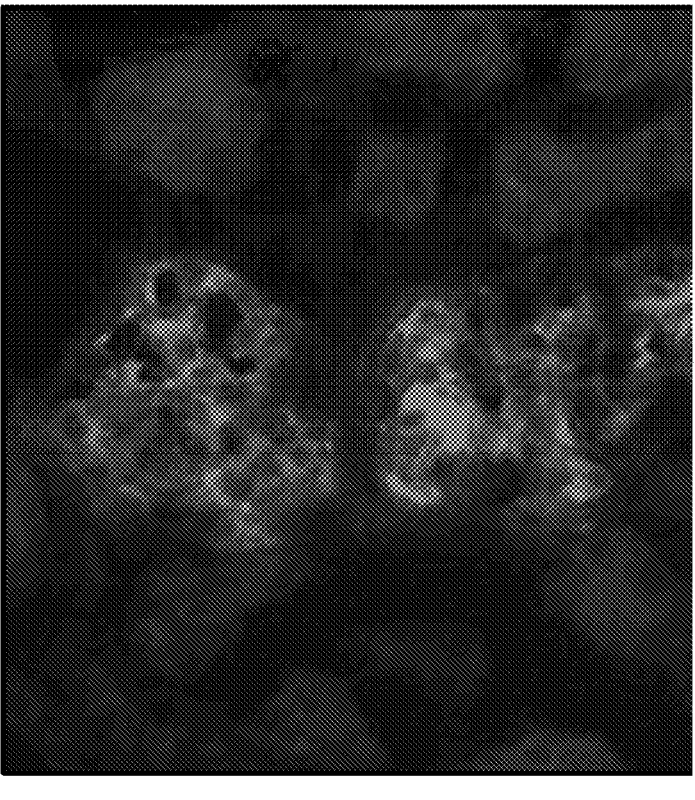

7 dially with PBS and the kidneys harvested and cryosectioned. The images shown in FIGS. 10A and 10B demonstrate that the antibody successfully targeted the endothelial cells in the glomeruli, which appear brightly labeled.

Figures 11A, 11B:
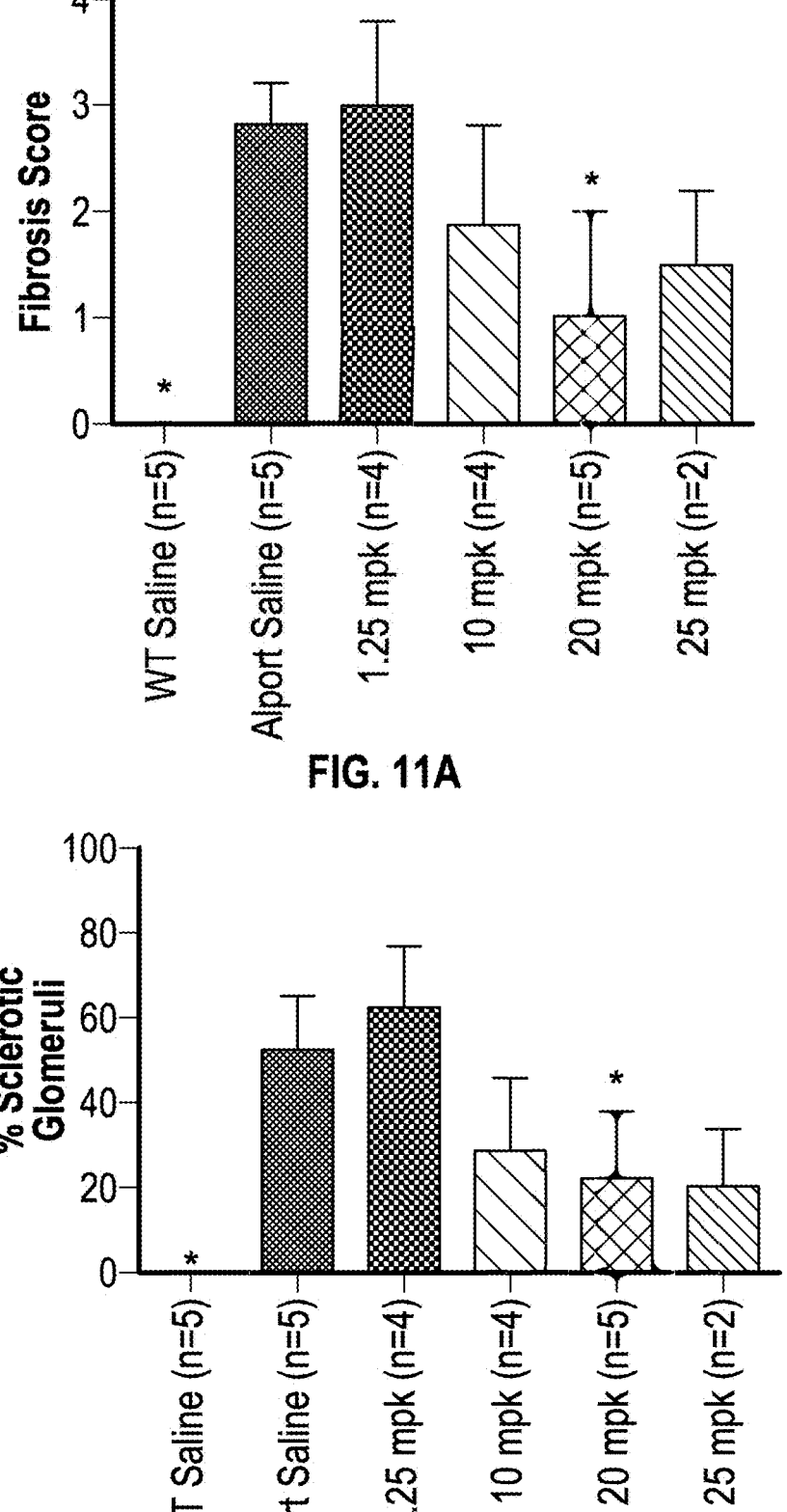

FIGS. 11A and 11B. 129 Sv/J autosomal Alport mice (4 per cohort) were treated with a function neutralizing antibody against ET-1 at the indicated doses from 2 to 7 weeks of age. Saline-treated Alport mice were used as controls. Cryosections were dual stained with anti-CD45 and collagen 1 and scored blinded for fibrosis (FIG. 11A) or stained with anti-fibronectin antibodies and scored blinded for % glomerulosclerosis (FIG. 11B). *=P<0.05.

Figure 12A:
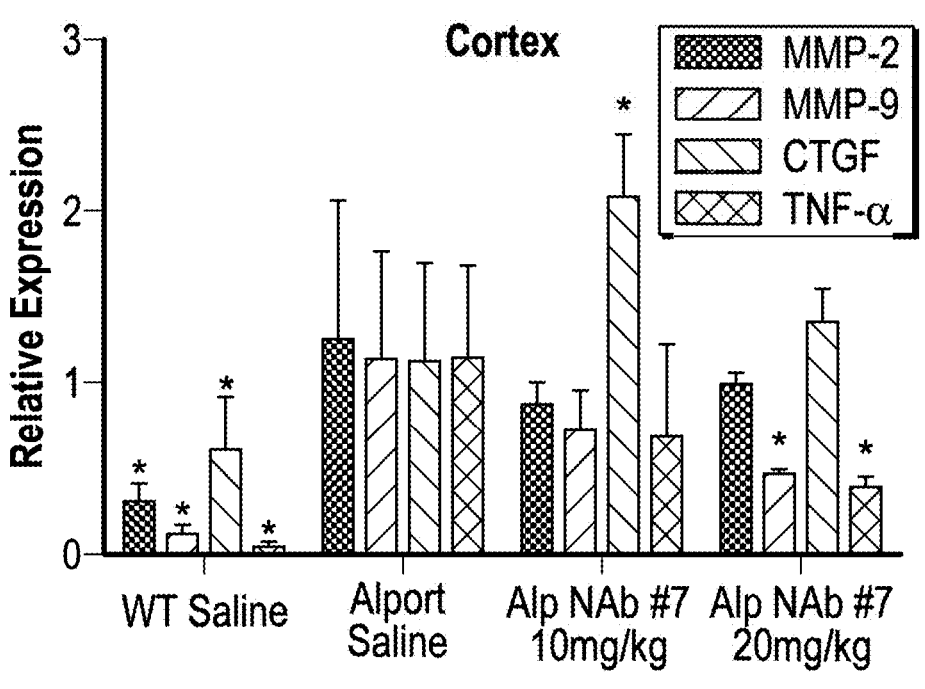
Figure 12B:
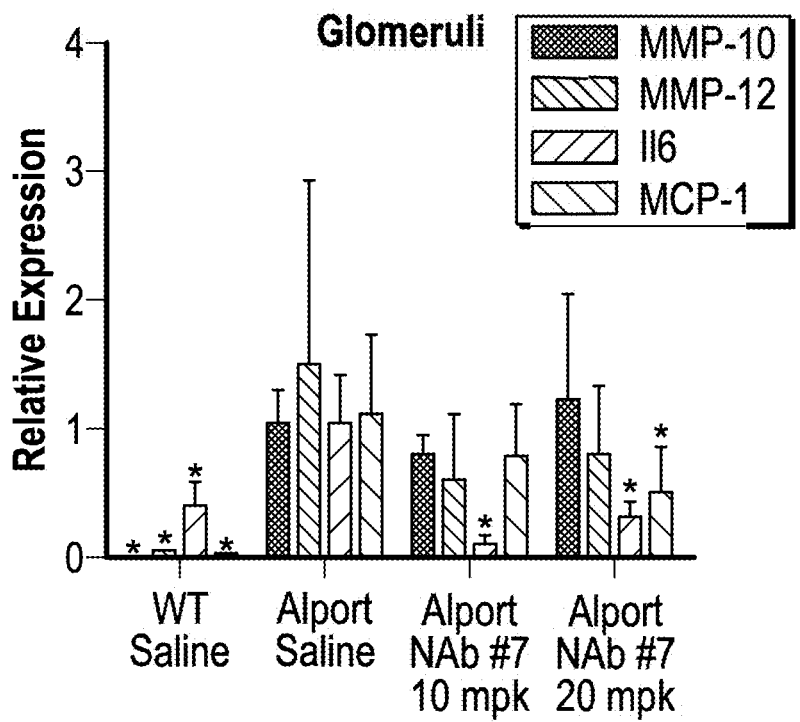

FIG. 12. RNA from the glomeruli and renal cortex from Alport mice treated with saline or the indicated doses of mAb #7 and analyzed by real time RT-PCR for the indicated transcripts.

Figure 13:
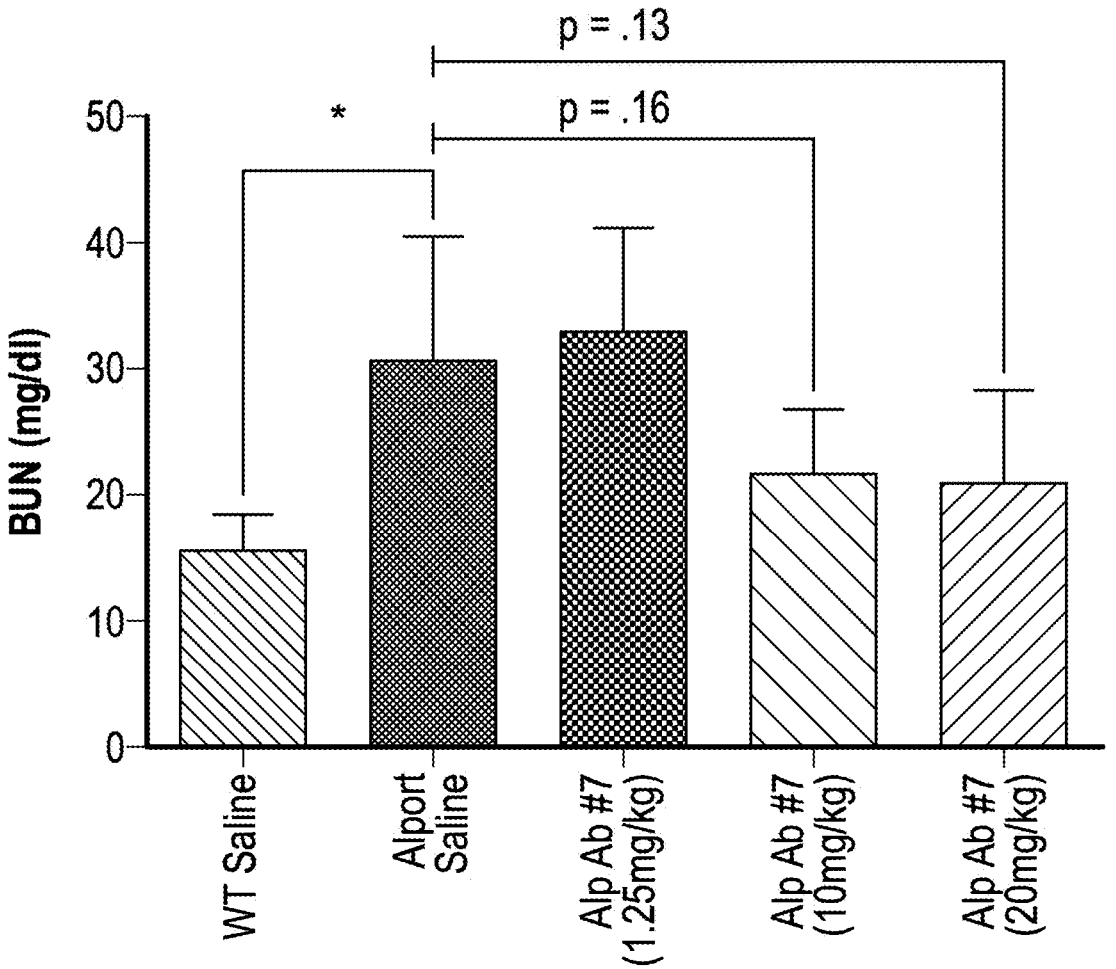

FIG. 13. BUN measures for treated mice are trending lower, however are not yet significant (n=4 for 0 mg/kg; n=5 for 10 mg/kg).

Figure 14:
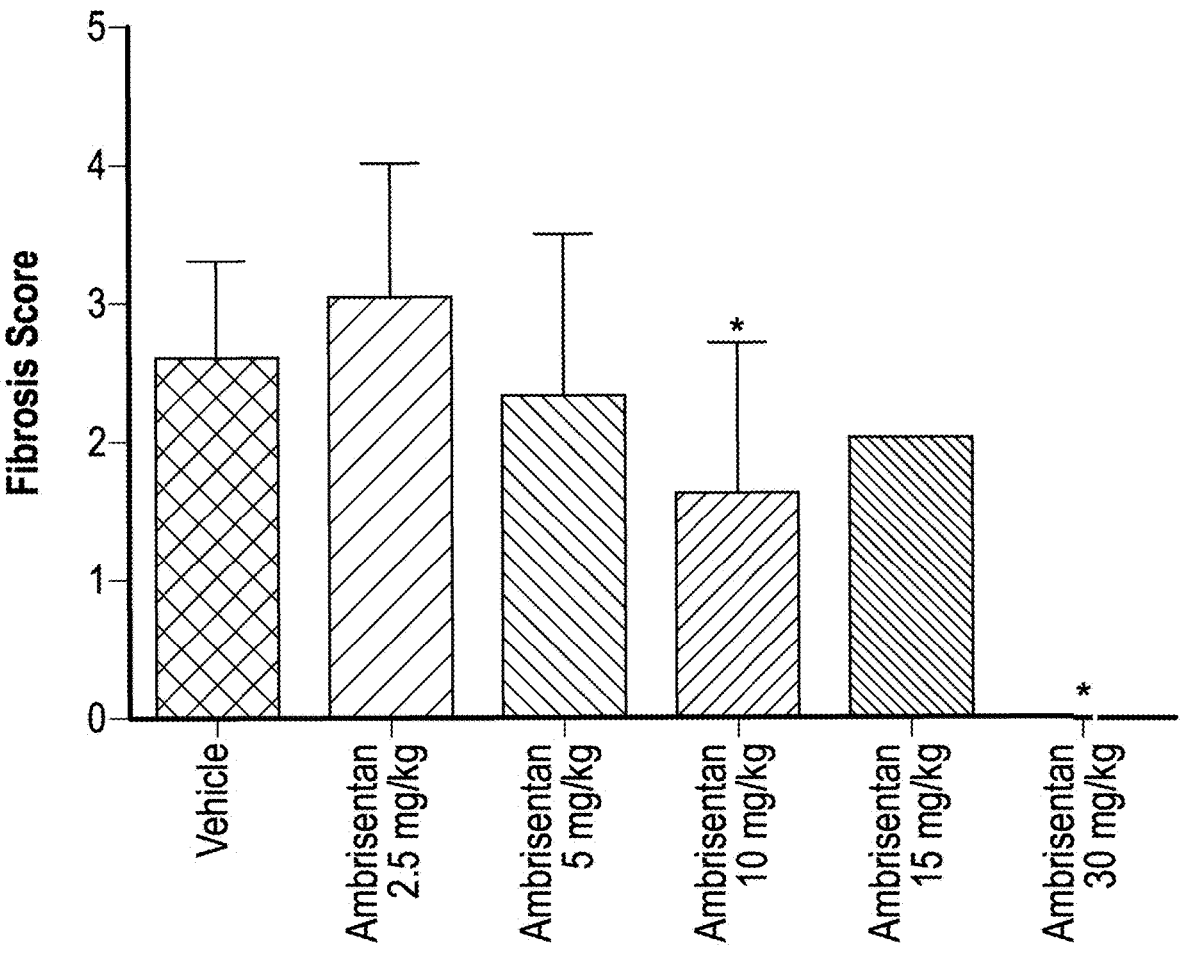

FIG. 14. Alport mice (3 per group) were treated by oral gavage daily with the indicated doses of Ambrisentan from 3 to 7 weeks of age, and the kidneys scored blinded for fibrosis scores.

Figure 15:
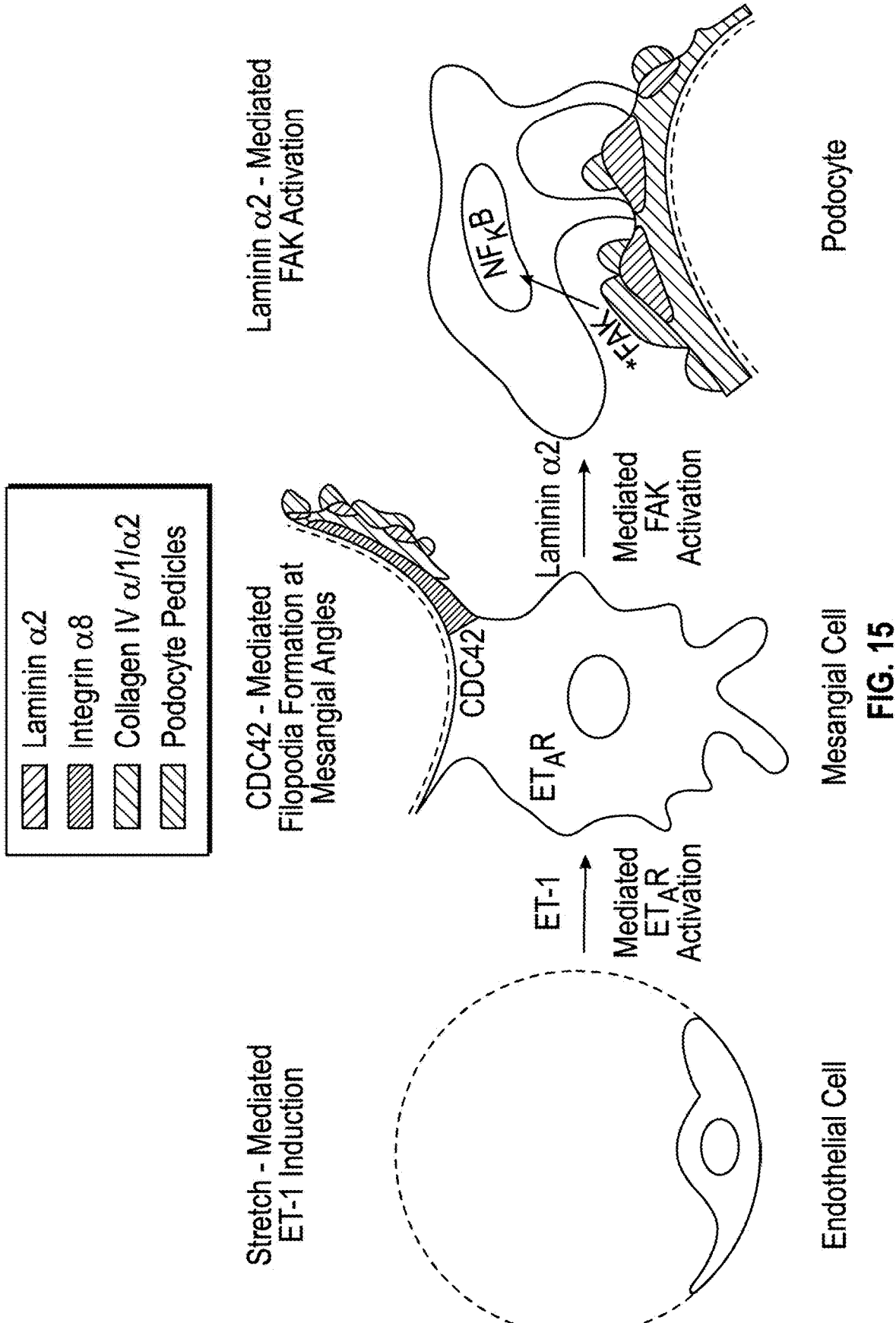

FIG. 15. Overview of mechanism for Alport glomerular disease initiation. The changes in GBM composition result in elevated biomechanical strain on all glomerular cells. In the endothelial cells, this results in elevated expression of endothelin-1, which activates the endothelin A receptors on mesangial cells. $ET_AR$ signaling in mesangial cells results in the activation of the small GTPase CDC42 which induces the formation of filopodia (shown in red) at the mesangial angles. These filopodia invade the sub-endothelial aspect of the GBM and deposit mesangial proteins in the GBM, including laminin α2 (shown in green). Laminin α2 activates focal adhesion kinase (*FAK) in the podocyte pedicles, which in turn activates NFkappaB, resulting in nuclear translocation and activation of pro-inflammatory genes (from Cosgrove and Liu, 2017, Matrix Biol; 57-58: 45-54).

FIG. 16. Power analysis for determining the number of animals per cohort required to detect statistically significant differences for the 129 Sv/J autosomal Alport syndrome model. For % sclerotic glomeruli (% SG), fibrosis scores (FS), albumin, BUN, and real time RT-PCR analysis for glomerular renal cortical disease markers, the aim is to detect differences between vehicle treated and neutralizing antibody treated Alport mice of 75%. This degree of reduction was previously exceeded by treatment with small molecule endothelin A receptor antagonists ((Dufek et al., 2016, Kidney Int; 90(2):300-310). Lifespan studies provide much tighter numbers, allowing a 25% increase in lifespan to be confidently detected in as few as six animals. Greater increases in lifespan are expected.

FIG. 17. Power analysis for determining the number of animals per cohort required to detect statistically significant differences for the C57Bl/6 XLAS model. For % sclerotic glomeruli (% SG), fibrosis scores (FS), albumin, BUN, and real time RT-PCR analysis for glomerular renal cortical disease markers, the aim is to detect differences between vehicle treated and neutralizing antibody treated Alport mice of 75%. This degree of reduction was previously exceeded by treatment with small molecule endothelin A receptor antagonists ((Dufek et al., 2016, Kidney Int; 90(2):300-310). Lifespan studies provide much tighter numbers, allowing a 25% increase in lifespan to be confidently detected in as few as six animals. Greater increases in lifespan are expected.

DETAILED DESCRIPTION

The present invention provides new biological therapeutic agents for use in the treatment of Alport syndrome and other conditions associated with endothelin-1 activation.

Alport syndrome (incidence about 1 in 5000) is characterized by delayed onset progressive glomerulonephritis associated with sensorineural hearing loss and retinal flecks (Kashtan and Michael, 1996, Kidney Int; 50 (5): 1445-1463). The most common form (80%) is X-linked and caused by mutations in the type IV collagen COL4A5 gene (Barker et al., 1990, Science; 248(4960):1224-7). The two autosomal forms of the disease account for the remaining 20% of Alport patients and result from mutations in the COL4A3 and COL4A4 genes (Mochizuki et al., 1994, Nat Genet; 8(1):77-81). The α3(IV), α4(IV) and α5(IV) proteins form a heterotrimer and are assembled into a subepithelial network in the mature glomerular basement membrane (GBM) that is physically and biochemically distinct from a subendothelial type IV collagen network comprised of α1(IV) and α2(IV) heterotrimers (Kleppel et al., 1992, J Biol Chem; 267(6):4137-4142). Mutation in any one of the three type IV collagen genes that cause Alport syndrome results in the absence of all three proteins in the glomerular basement membrane (GBM) due to an obligatory association in basement membrane collagen assembly to form functional heterotrimers (Kalluri and Cosgrove, 2000, J Biol Chem; 275(17):12719-12724). Thus, the net result for all genetic forms of Alport syndrome is the absence of the α3(IV) α4(IV) α5(IV) subepithelial collagen network, resulting in a thinner GBM type IV collagen network comprised only of α1(IV) and α2(IV) heterotrimers.

This change in basement membrane composition does not result in immediate pathology. The GBM appears to function adequately for the first few years of life and sometimes past the first decade (Kashtan et al., 1998, Pediatr Nephrol; 12(4):269-27). This delayed onset predicts a triggering mechanism for glomerular disease initiation and a theoretical window for therapeutic intervention that may arrest or significantly ameliorate Alport renal disease in its earliest stages. One of the earliest events documented is the appearance of an irregular deposition of laminin 211 in the GBM of Alport mice (Cosgrove et al., 2000, Am J Pathol; 157 (5):1649-59), an observation confirmed in both Alport dogs and human patients with the disease (Kashtan et al., 2001, J Am Soc Nephrol; 12:252-60).

Since the α1(IV)/α2(IV) collagen network contains significantly fewer interchain disulfide crosslinks (Gunwar et al., 1998, J Biol Chem; 273(15):8767-75), and since the Alport GBM is thinner than normal (Kamenetsky et al., 2010, J Digital Imaging; 23:463-474), the Alport GBM is likely to be more elastic than mature wild type GBM, resulting in elevated biomechanical strain on the glomerular cells at their points of contact with the GBM. Consistent with this, glomeruli from pre-proteinuric Alport mice have been shown to have elevated deformability relative to wild type glomeruli (Wyss et al., 2011, Am J Physiol Cell Physiol; 300:C397-C405), and salt-induced hypertension has been shown to accelerate glomerular disease progression in Alport mice (Meehan et al., 2009, Kidney Int; 76:968-976), suggesting strain-mediated responses can drive glomerular pathology.

A role for endothelin-1 (ET-1) activation of endothelin A receptors (ETARs) in the glomerular pathogenesis of Alport syndrome has been recently shown. Endothelin 1 is induced in the endothelial cells of Alport mice before the onset of proteinuria, and this expression is further induced by hypertension (Dufek et al., 2016, *Kidney Int;* 90(2):300-310). It has also been shown that ET-1 treatment of primary cultured mesangial cells activates CDC42 and induces the formation of drebrin-positive actin microspikes, consistent with the activation of filopodia (Zallocchi et al., 2013, *Am J Pathol;* 183(4):1269-80). If this formation of filopodia is blocked by way of a small molecule inhibitor for RAC1/CDC42 Rho GTPases (NCS 23766), laminin 211 deposition in the Alport GBM is largely blocked (Zallocchi et al., 2013, *Am J Pathol;* 183(4):1269-80).

Similarly, when endothelin A receptors in Alport mice are blocked with the small molecule ET-1 inhibitor Sitaxentan, markedly reduced mesangial process invasion of the glomerular capillaries is observed, as well as delayed the onset and progression of proteinuria, ameliorated GBM structural abnormalities, and significantly reduced glomerular expression of MMPs and pro-inflammatory cytokines (Dufek et al., 2016, *Kidney Int;* 90(2):300-310); U.S. Pat. No. 9,719,981; and International Publication No. WO 2014/028059). Collectively, these studies define a molecular mechanism that is key to the initiation of glomerular pathology in Alport syndrome. This mechanism has been recently confirmed in a dog model for Alport syndrome (Clark et al., 2016, *PLoS One;* 11(12):e0168343), demonstrating that this mechanism is not specific to the mouse model.

FIG. 15 provides an overview of the mechanism for Alport glomerular disease initiation. The changes in GBM composition result in elevated biomechanical strain on all glomerular cells. In the endothelial cells, this results in elevated expression of endothelin-1, which activates the endothelin A receptors on mesangial cells. $ET_AR$ signaling in mesangial cells results in the activation of the small GTPase CDC42 which induces the formation of filopodia at the mesangial angles. These filopodia invade the sub-endothelial aspect of the GBM and deposit mesangial proteins in the GBM, including laminin $\alpha2$. Laminin $\alpha2$ activates focal adhesion kinase (*FAK) in the podocyte pedicles, which in turn activates NFkappaB, resulting in nuclear translocation and activation of pro-inflammatory genes (from Cosgrove and Liu, 2017, *Matrix Biol;* 57-58:45-54).

Small molecule endothelin-1 antagonists, such as bosentan, sitaxsentan, ambrisentan, and macitentan, sparsentan, and altrasentan have revolutionized the treatment of diseases such as pulmonary arterial hypertension (PAH) (see, for example, Dupuis and Hoeper, 2008, *European Respiratory Journal;* 31:407-415; Chester and Yacoub, 2014, *Glob Cardiol Sci Pract;* 2014(2): 62-78; Grune and Kuebler, 2018, *European Respiratory Journal;* 52:1801287; and Davenport et al., 2016, *Pharmacol Rev;* 68(2):357-418). However, these small molecule inhibitors are notoriously toxic with significant off target effects. For example, sitaxentan was marketed as THELIN® for the treatment of pulmonary arterial hypertension (PAH), until Pfizer voluntarily removed it from the market in 2010 due to concerns about liver toxicity. These toxicities preclude their use for the treatment of chronic kidney diseases such as Alport syndrome, especially in children.

Disclosed herein, for the first time, are antibodies to endothelin-1 effective for use as therapeutic agents for delaying the onset and progression of pathologies associated with endothelin-1 activation, including, but not limited to, delaying the onset and progression of glomerular disease and sensorineural hearing loss associated with Alport syndrome.

An antibody of the present invention may specifically bind to endothelin-1, including human endothelin-1. Endothelin-1 (ET-1) is a potent vasoactive peptide first identified in 1988. Originally isolated from porcine aortic endothelial cells, ET-1 is one of a family of three isomers also including endothelin-2 (ET-2) and endothelin-3 (ET-3). ET-1 is a peptide of 21 amino acid residues in length. All of the endothelin family members are synthesized initially as prepropolypeptides of approximately 200 amino acid residues encoded by separate genes. These are proteolytically cleaved to produce biologically-inactive propolypeptides of approximately 40 amino acid which are then cleaved by the proteolytic action of a membrane-bound metalloprotease to produce the 21 amino acid residue active peptide. Human endothelin-1 has the amino acid sequence Cys-Ser-Cys-Ser-Ser-Leu-Met-Asp-Lys-Glu-Cys-Val-Tyr-Phe-Cys-His-Leu-Asp-Ile-Ile-Trp (SEQ ID NO:1). The structure of ET-1 is unusual among the mammalian bioactive peptides in possessing two essential intramolecular disulfide bonds between Cys residues crosslinked at positions 1 and 15 and 3 and 11. See, for example, Yanagisawa et al., 1988, *Proc Natl Acad Sci USA;* 85(18):6964-7; Xu et al., 1994, *Cell;* 78:473; and Davenport et al., 2016, *Pharmacol Rev;* 68(2): 357-418.

Antibodies of the present invention may "specifically bind to" or be "specific for" a particular polypeptide, such as endothelin-1, or an epitope on a particular polypeptide. Such an antibody is one that binds to that particular polypeptide or epitope on a particular polypeptide without substantially binding to any other polypeptide or polypeptide epitope. Antibodies of the present invention can be assayed for immunospecific binding by the methods described herein and by any suitable method known in the art. The immunoassays that can be used include, but are not limited to, competitive and non-competitive assay systems using techniques such as BIAcore analysis, fluorescence activated cell sorter (FACS) analysis, immunofluorescence, immunocytochemistry, Western blots, radio-immunoassays, enzyme linked immunosorbent assay (ELISA), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. Such assays are routine and well known in the art.

An antibody of the present invention may be a neutralizing antibody, neutralizing one or more functions of endothelin-1, including, for example, neutralizing one or more of the functions as detailed in the examples section included herewith.

For example, a neutralizing antibody of the present invention may characterized in a mesangial cell-based bioassay, inhibiting the formation of drebrin-positive actin microspikes and/or blocking the formation of filopodia in primary cultured mesangial cells treated with ET-1 (Dufek et al., 2016, *Kidney Int;* 90(2):300-310); United U.S. Pat. No. 9,719,981; and International Publication No. WO 2014/028059).

A neutralizing antibody of the present invention may be characterized in a biochemical assay for actin polymerization. ET-1 treatment of cultured mesangial cells induces the formation of filamentous actin (F-actin). This can be measured by pelleting the F-actin and measuring the ratio of F-actin to globular actin (G-actin), the latter, which remains in the supernatant. Inclusion of function neutralizing antibodies prevents the ET-1 induced formation of F-actin. In some aspects, the degree to which F-actin polymerization is inhibited (% reduction of ET-1 F/G ratio) is indicative of the efficacy of the function neutralizing capacity of the antibody.

A neutralizing antibody of the present invention may characterized in vivo, in animal model systems of Alport syndrome, such as the 129Sv/J autosomal Alport mouse or the dog model for Alport syndrome (Clark et al., 2016, *PLoS One;* 11(12):e0168343). Inhibition of one or more of pathologies may be observed, such as for example, reduction of glomerular pathology, reduction in fibrosis scores, reduction of glomerulosclerosis, reduction of mesangial process invasion of the glomerular capillaries, delayed onset and/or progression of proteinuria, amelioration GBM structural abnormalities, reduction of glomerular expression of MMPs and/or reduction of glomerular expression of MMPs pro-inflammatory cytokines (Dufek et al., 2016, *Kidney Int;* 90(2):300-310); United U.S. Pat. No. 9,719,981; and International Publication No. WO 2014/028059).

An antibody of the present invention may be a polyclonal antibody or a monoclonal antibody. In preferred embodiments, an antibody of the present invention is a monoclonal antibody. The term "monoclonal antibody" or "monoclonal antibody composition," as used herein, refers to a homogeneous population of antibodies. All of the antibodies in the preparation recognize the same epitope on the target molecule and all of the monoclonal antibodies have the same affinity. As used herein the terms "monoclonal antibody" or "monoclonal antibodies" are used interchangeably.

Representative anti-endothelin-1 antibodies of the present invention include, but are not limited to:

monoclonal Antibody #1 (also referred to herein as "Aby #1," "mAb #1, and "Nab #1") produced by the hybridoma cell line Nab #1 5D 1087 deposited at the American Type Culture Collection (ATCC[[®]]), 10801 University Boulevard, Manassas, Va. 20110-2209, USA, on Mar. 28, 2019, under Patent Designation PTA-125819;

monoclonal Antibody #7 (also referred to herein as "Aby #7," "mAb #7, and "Nab #7") produced by the hybridoma cell line Nab #7 3G 9A4 deposited at the American Type Culture Collection (ATCC[[®]]), 10801 University Boulevard, Manassas, Va. 20110-2209, USA, on Mar. 28, 2019, under Patent Designation PTA-125818; and monoclonal Antibody #15 (also referred to herein as "Aby #15," "mAb #15, and "Nab #15") produced by the hybridoma cell line Nab #15 7D 489 deposited at the American Type Culture Collection (ATCC[[®]]), 10801 University Boulevard, Manassas, Va. 20110-2209, USA, on Mar. 28, 2019, under Patent Designation PTA-125817.

Such ATCC[[®]] deposit may be in accordance with the Budapest Treaty on the International Recognition of the Deposit of Microorganisms for the Purposes of Patent Procedure.

An intact antibody molecule has two heavy (H) chains and two light (L) chains. Each heavy chain has the same heavy chain variable region (VH) and each light chain has the same light chain variable region (VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al., *J. Mol. Biol.* 1987; 196:901-917). Each VH and VL is composed of three CDR's and four FRs, arranged from amino-terminus to carboxy-terminus in the following order: FR1, CDR1, FR2, CDR2, FR3, CDR3, FR4.

The present invention includes an antibody with the same heavy chain and/or light chain of a monoclonal antibody described above. Such an antibody may bind endothelin-1, including but not limited to, human endothelin-1. Such an antibody may be a neutralizing antibody, neutralizing one of more functions of endothelin-1, including but not limited to, human endothelin-1.

The present invention includes an antibody with the heavy chain variable (VH) regions and/or the light chain variable (VL) regions of a monoclonal antibody described above. Such an antibody may bind endothelin-1, including, but not limited to human endothelin-1. Such an antibody may be a neutralizing antibody, neutralizing one of more functions of endothelin-1, including, but not limited to human endothelin-1.

The present invention includes an antibody with the one or more of the CDRs of a monoclonal antibody described above. For example, including one, any two, or all three of the heavy chain CDRs and/or one, any two, or all three of the light chain CDRs. Such an antibody may bind endothelin-1, including, but not limited to human endothelin-1. Such an antibody may be a neutralizing antibody, neutralizing one of more functions of endothelin-1, including, but not limited to human endothelin-1.

Methods for determining the DNA and amino acid sequences of monoclonal antibodies produced by human, mouse, and rat hybridoma cell lines are well known. See, for example, Babrak et al., 2017, *Molecular Immunology;* 90:287-294; Bialon et al., 2014, *Monoclon Antib Immunodiagn Immunother;* 33:369-377; Burkovitz and Ofran, 2016, *Mabs;* 8:278-287; Cochet et al., 1999, *Biotechniques;* 26:818-820; de Marco, 2015, *Microb Cell Fact;* 14:125; Doenecke et al., 1997, *Leukemia;* 11:1787-1792; Georgiou, 2014, *Nature Biotechnology;* 32(2):158-168; Jarasch and Skerra, 2017, *Proteins;* 85:65-71; Kolawole et al., 2014, *J Virol;* 88(8):4543-57; Kuniyoshi et al., 2016, *PLoS One;* 11:e0165473; Lefranc, 2014, *Microbiol Spectr;* 2; Martinez-Navio and Desrosiers, 2012, *J Virol;* 86(23):12484-93; Lo et al., 2014, *Microbiol Spectr;* 2; Orlandi et al., 1989, *Proc Natl Acad Sci USA;* 86:3833-3837; Schanz et al., 2014, *PLoS One;* 9: e111726; Wang et al., 2000, *J Immunol Methods;* 233:167-177; and Wang et al., 2013, *J Virol;* 87(16):8909-15.

Commercial services are available to undertake such sequencing, including, but not limited to, such commercial services as Abzena, San Diego, CA; Absolute Antibody, Oxford, UK; Antibody Design Laboratories, San Diego, CA; Creative Biolabs, (world wide web site creative-biolabs.com); Fusion Antibodies; Genscript; ProMab Biotechnologies, Inc.; and Syd Labs, Malden, MA.

Using any such methods, the nucleotide sequences and the encoded amino acid sequences of the heavy chain and/or light chain, the heavy chain variable (VH) region and/or the light chain variable (VL) region, and all three of the heavy chain CDRs and/or all three of the light chain CDRs of a given monoclonal antibody, including but not limited to, monoclonal Antibody #1 produced by the hybridoma cell line Nab #1 5D 1087 deposited at ATCC[[®]] under Patent Designation PTA-125819, monoclonal Antibody #7 produced by the hybridoma cell line Nab #7 3G 9A4 deposited at the ATCC[[®]] under Patent Designation PTA-125818, and monoclonal Antibody #15 produced by the hybridoma cell line Nab #15 7D 489 deposited at the ATCC[[®]] under Patent Designation PTA-125817, may be determined.

Antibody #1

The present invention also includes an antibody and antigen binding fragments thereof that binds to the same epitope of human endothelin-1 that is recognized by monoclonal Antibody #1 produced by the hybridoma cell line Nab #1 5D 1087 deposited at the ATCC[[®]] under Patent Designation PTA-125819

Also included in the present invention are antibodies and antigen binding fragments thereof that have the same heavy (H) chain polypeptide sequence as monoclonal Antibody #1, the same light (L) chain polypeptide sequence as monoclonal Antibody #1, or the same heavy chain polypeptide sequence and the same light chain polypeptide sequence as monoclonal Antibody #1. Such antibodies may contain one, two, three, four, five, six, or more amino acid substitutions in the heavy and/or the light chains.

Also included in the present invention are antibodies and antigen binding fragments thereof that have the same heavy chain variable (VH) region polypeptide sequence as monoclonal Antibody #1, the same light chain variable (VL) region polypeptide sequence as monoclonal Antibody #1, or the same VH region polypeptide sequence and the same VL region polypeptide sequence as monoclonal Antibody #1. Such antibodies may contain one, two, three, four, five, six, or more amino acid substitutions in the heavy and/or the light chains.

The present invention also includes antibodies and antigen binding fragments thereof having an amino acid sequence at least about 70%, at least about 80%, at least about 85%, at least about 90%, at least about 95%, at least about 96%, at least about 97%, at least about 98%, or at least about 99% identical to the VH region polypeptide sequence as monoclonal Antibody #1 and/or having an amino acid sequence at least about 70%, at least about 80%, at least about 85%, at least about 90%, at least about 95%, at least about 96%, at least about 97%, at least about 98%, or at least about 99% identical to the VL region polypeptide sequence as monoclonal Antibody #1. As used herein "sequence identity" between two polypeptides is determined by comparing the amino acid sequence of one polypeptide to the sequence of a second polypeptide. When discussed herein, whether any particular polypeptide is at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

The present invention also includes antibodies and antigen binding fragments thereof having one or more of the complementarity determining regions (CDRs) of the heavy chain of monoclonal Antibody #1. In some embodiments, the antibody and antigen binding fragments thereof further include a light chain variable region having one or more of the CDRs of the light chain of monoclonal Antibody #1. For example an antibody or and antigen binding fragment thereof may have at least one CDR region of the VH domain of monoclonal Antibody #1; at least two CDR regions of the VH domain of monoclonal Antibody #1; or all three CDR regions of the VH domain of monoclonal Antibody #1 and/or at least one CDR region of the VL domain of monoclonal Antibody #1; at least two CDR regions of the VL domain of monoclonal Antibody #1; or all three CDR regions of the VL domain of monoclonal Antibody #1. Also included are such antibodies and antigen binding fragments thereof having one, two, three, four, five, six, or more amino acid substitutions in one or more CDR regions.

Antibody #7

The present invention also includes an antibody and antigen binding fragments thereof that binds to the same epitope of human endothelin-1 that is recognized by monoclonal Antibody #7 produced by the hybridoma cell line Nab #7 3G 9A4 deposited at the ATCC[[®]] under Patent Designation PTA-125818.

Also included are antibodies and antigen binding fragments thereof that have the same heavy (H) chain polypeptide sequence as monoclonal Antibody #7, the same light (L) chain polypeptide sequence as monoclonal Antibody #7, or the same heavy chain polypeptide sequence and the same light chain polypeptide sequence as monoclonal Antibody #7. The present invention also includes such antibodies containing one, two, three, four, five, six, or more amino acid substitutions in the heavy and/or the light chains.

Also included in the present invention are antibodies and antigen binding fragments thereof that have the same heavy chain variable (VH) region polypeptide sequence as monoclonal Antibody #7, the same light chain variable (VL) region polypeptide sequence as monoclonal Antibody #7, or the same VH region polypeptide sequence and the same VL region polypeptide sequence as monoclonal Antibody #7. The present invention also includes such antibodies containing one, two, three, four, five, six, or more amino acid substitutions in the heavy and/or the light.

The present invention also includes antibodies and antigen binding fragments thereof having an amino acid sequence at least about 70%, at least about 80%, at least about 85%, at least about 90%, at least about 95%, at least about 96%, at least about 97%, at least about 98%, or at least about 99% identical to the VH region polypeptide sequence as monoclonal Antibody #7 and/or having an amino acid sequence at least about 70%, at least about 80%, at least about 85%, at least about 90%, at least about 95%, at least about 96%, at least about 97%, at least about 98%, or at least about 99% identical to the VL region polypeptide sequence as monoclonal Antibody #7.

The present invention also includes antibodies and antigen binding fragments thereof having one or more of the complementarity determining regions (CDRs) of the heavy chain of monoclonal Antibody #7. In some embodiments, the antibody and antigen binding fragments thereof further include a light chain variable region having one or more of the CDRs of the light chain of monoclonal Antibody #7. For example an antibody or and antigen binding fragment thereof may have at least one CDR region of the VH domain of monoclonal Antibody #7; at least two CDR regions of the VH domain of monoclonal Antibody #7; or all three CDR regions of the VH domain of monoclonal Antibody #7 and/or at least one CDR region of the VL domain of monoclonal Antibody #7; at least two CDR regions of the VL domain of monoclonal Antibody #7; or all three CDR regions of the VL domain of monoclonal Antibody #7. Also included are such antibodies and antigen binding fragments thereof having one, two, three, four, five, six, or more amino acid substitutions in one or more CDR regions.

Antibody #15

The present invention also includes an antibody and antigen binding fragments thereof that binds to the same epitope of human endothelin-1 that is recognized by monoclonal Antibody #15 produced by the hybridoma cell line Nab #15 7D 489 deposited at the ATCC[[®]] under Patent Designation PTA-125817.

Also included in the present invention are antibodies and antigen binding fragments thereof that have the same heavy (H) chain polypeptide sequence as monoclonal Antibody #15, the same light (L) chain polypeptide sequence as monoclonal Antibody #15, or the same heavy chain polypeptide sequence and the same light chain polypeptide sequence as monoclonal Antibody #15. The present invention also includes such antibodies containing one, two, three, four, five, six, or more amino acid substitutions in the heavy and/or the light chains.

Also included in the present invention are antibodies and antigen binding fragments thereof that have the same heavy chain variable (VH) region polypeptide sequence as monoclonal Antibody #15, the same light chain variable (VL) region polypeptide sequence as monoclonal Antibody #15, or the same VH region polypeptide sequence and the same VL region polypeptide sequence as monoclonal Antibody #15. The present invention also includes such antibodies containing one, two, three, four, five, six, or more amino acid substitutions in the heavy and/or the light chains.

The present invention also includes antibodies and antigen binding fragments thereof having an amino acid sequence at least about 70%, at least about 80%, at least about 85%, at least about 90%, at least about 95%, at least about 96%, at least about 97%, at least about 98%, or at least about 99% identical to the VH region polypeptide sequence as monoclonal Antibody #15 and/or having an amino acid sequence at least about 70%, at least about 80%, at least about 85%, at least about 90%, at least about 95%, at least about 96%, at least about 97%, at least about 98%, or at least about 99% identical to the VL region polypeptide sequence as monoclonal Antibody #15.

The present invention also includes antibodies and antigen binding fragments thereof having one or more of the complementarity determining regions (CDRs) of the heavy chain of monoclonal Antibody #15. In some embodiments, the antibody and antigen binding fragments thereof may further include a light chain variable region having one or more of the CDRs of the light chain of monoclonal Antibody #15. For example an antibody or and antigen binding fragment thereof may have at least one CDR region of the VH domain of monoclonal Antibody #15; at least two CDR regions of the VH domain of monoclonal Antibody #15; or all three CDR regions of the VH domain of monoclonal Antibody #15 and/or at least one CDR region of the VL domain of monoclonal Antibody #15; at least two CDR regions of the VL domain of monoclonal Antibody #15; or all three CDR regions of the VL domain of monoclonal Antibody #15. Also included are such antibodies and antigen binding fragments thereof having one, two, three, four, five, six, or more amino acid substitutions in one or more CDR.

The antibodies of the present invention can be of any type (such as, for example, IgG, IgE, IgM, IgD, IgA and IgY), class (such as, for example, IgG1, IgG2, IgG3, IgG4, IgAQ1 and IgA2) or subclass of immunoglobulin molecule. In some embodiments, the immunoglobulin is an IgG. An array of IgG, IgE, IgM, IgD, IgA, and IgY heavy chains can be paired with a light chain of the kappa or lambda form.

The antibodies of the invention can be from any animal origin, including birds and mammals. In some embodiments, the antibodies are human, murine, rat, donkey, sheep, rabbit, goat, guinea pig, camel, horse, llama, camel, or chicken antibodies.

Antibodies of the present invention may include dimeric, trimeric, and multimeric antibodies, bispecific antibodies, chimeric antibodies, human antibodies, humanized antibodies, recombinant antibodies, and engineered antibodies.

In certain embodiments, an antibody is "humanized." Humanized monoclonal antibodies are produced by transferring one or more CDRs from the heavy and light variable chains of a mouse (or other species) immunoglobulin into a human variable domain, then substituting human residues into the framework regions of the murine counterparts. The use of antibody components derived from humanized monoclonal antibodies obviates potential problems associated with immunogenicity of murine constant regions. Techniques for producing humanized monoclonal antibodies can be found, for example, in Jones et al., 1986, *Nature;* 321:522 and Singer et al., 1993, *J Immunol:* 150:2844. The constant region of a humanized monoclonal antibody of the present invention can be that from human immunoglobulin belonging to any isotype. It may be, for example, the constant region of human IgG. The framework regions of the constant region derived from human immunoglobulin are not particularly limited.

Entirely human antibodies may also be prepared and used in the present invention. Such human antibodies may be obtained, for example, from healthy subjects by obtaining a population of mixed peripheral blood lymphocytes from a human subject or isolated from human immunoglobulin libraries or from animals transgenic for one or more human immunoglobulins.

The present invention also includes various antibody fragments, also referred to as antigen binding fragments, which include only a portion of an intact antibody, generally including an antigen binding site of the intact antibody and thus retaining the ability to bind antigen. The techniques for preparing and using various antibody-based constructs and fragments are well known in the art. For example, fragments can be obtained via chemical or enzymatic treatment of an intact or complete antibody or antibody chain. Fragments can also be obtained by recombinant means. Examples of antibody fragments include, for example, Fab, Fab', F(ab')$_2$, Fd, Fd', scFv (single chain Fv), single domain antibodies (dAB), linear antibodies, diabodies, and the like.

Antibodies of the present invention may be isolated. "Isolated," when used to describe the various antibodies disclosed herein, means the antibody that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes.

Antibodies of the present invention can be produced by an animal, cultured cell line, chemically synthesized, or recombinantly expressed. Monoclonal antibodies of the present invention can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, NY (1989).

The antibodies of the present invention may be coupled directly or indirectly to a detectable marker by techniques well known in the art. A detectable marker is an agent detectable, for example, by spectroscopic, photochemical, biochemical, immunochemical, or chemical means. Useful detectable markers include, but are not limited to, fluorescent dyes, chemiluminescent compounds, radioisotopes, electron-dense reagents, enzymes, colored particles, biotin, or dioxigenin. A detectable marker often generates a measurable signal, such as radioactivity, fluorescent light, color, or enzyme activity. Antibodies conjugated to detectable agents may be used for diagnostic or therapeutic purposes. Examples of detectable agents include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the antibody or indirectly, through an intermediate such as, for example, a linker known in the art, using techniques known in the art. See, for example, U.S. Pat. No. 4,741,900, describing the conjugation of metal ions to antibodies for diagnostic use. Examples of suitable enzymes include horseradish peroxidase, alkaline phosphatase, beta-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; examples of bioluminescent materials include luciferin, and aequorin; and examples of suitable radioactive material include iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113}$mIn, $^{115}$mIn), technetium ($^{99}$Tc, $^{99}$mTc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru. Techniques for conjugating such moieties to antibodies are well-known.

Antibodies of the present invention include derivatives of antibodies that are modified or conjugated by the covalent attachment of any type of molecule to the antibody. Such antibody derivatives include, for example, antibodies that have been modified by glycosylation, acetylation, pegylation, phosphorylation, amidation, derivatization by known protecting/blocking groups, proteolytic cleavage, or linkage to a cellular ligand or other protein. Any of numerous chemical modifications can be carried out by known techniques, including, but not limited to, specific chemical cleavage, acetylation, formylation, and metabolic synthesis of tunicamycin. Additionally, the derivatives can contain one or more non-classical amino acids.

In some embodiments, additional modifications may be made to antibodies or functional parts described herein to improve their serum half-life. For example, mutations such as deletion, addition, or substitution mutations may be made to the antibodies or functional parts to improve their half-life. In some embodiments, the Fc region may be mutated to include one, two, or all three of the following substitutions M252Y, S254T, and T256E, wherein the numbering corresponds to the EU index in Kabat. In one embodiment, the Fc region may be mutated to include all three of the following substitutions M252Y, S254T, and T256E, wherein the numbering corresponds to the EU index in Kabat, referred to as the YTE variant. See, for example, Dall'Acqua et al., 2006, *J Biol Chem;* 281(33):23514-23524.

Antibodies of the present invention include antibodies that have undergone affinity maturation and/or optimization. Several companies provide services to perform the affinity maturation and humanization of monoclonal antibodies, including, for example Creative BioLabs.

Once an antibody or functional part thereof has been produced, it may be purified by any method known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification or detection.

The invention also provides a kit including one or more antibodies of the present invention. The kit may include one or more containers filled with one or more of the antibodies of the invention. Additionally, the kit may include other reagents such as buffers and solutions needed to practice the invention are also included. Optionally associated with such container(s) can be a notice or printed instructions. A kit can include packaging material. As used herein, the phrase "packaging material" refers to one or more physical structures used to house the contents of the kit. The packaging material is constructed by well known methods, preferably to provide a sterile, contaminant-free environment.

Also included in the present invention are compositions including one or more of the antibodies described herein. A composition may also include, for example, buffering agents to help to maintain the pH in an acceptable range or preservatives to retard microbial growth. A composition may include, for example, carriers, excipients, stabilizers, chelators, salts, or antimicrobial agents. Acceptable carriers, excipients, stabilizers, chelators, salts, preservatives, buffering agents, or antimicrobial agents, include, but are not limited to, buffers such as phosphate, citrate, and other organic acids; antioxidants including ascorbic acid and methionine; preservatives, such as sodium azide, octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol; polypeptides; proteins, such as serum albumin, gelatin, or non-specific immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (for example, Zn-protein complexes); and/or non-ionic surfactants such as TWEEN® (polysorbate), PLURONIC® (poloxamer), or polyethylene glycol (PEG). As used herein, a composition is not a polyclonal antiserum.

Also included in the present invention are hybridoma cell lines, transformed B cell lines, and host cells that produce the monoclonal antibodies of the present invention; the progeny or derivatives of these hybridomas, transformed B cell lines, and host cells; and equivalent or similar hybridomas, transformed B cell lines, and host cells. Progeny or derivatives thereof may produce an antibody with one or more of the identifying characteristics, such as, for example, isotype and antigen specificity, of the antibody produced by the parental line.

DNA/Vectors

The present invention further provides an isolated polynucleotide molecule having a nucleotide sequence encoding an antibody of the invention, or a portion thereof. The present invention is further directed to an isolated polynucleotide molecule having a nucleotide sequence that has at least 75%, at least 80%, at least 85%, at least 90%, at least 95%, at least 96%, at least 97%, at least 98%, or at least 99% sequence identity to nucleotide sequence encoding an antibody of the invention, or a portion thereof. The invention also encompasses polynucleotides that hybridize under high stringency to a nucleotide sequence encoding an antibody of the invention, or a complement thereof. As used herein "stringent conditions" refer to the ability of a first polynucleotide molecule to hybridize, and remain bound to, a second, filter-bound polynucleotide molecule in 0.5 M NaHPO$_4$, 7% sodium dodecyl sulfate (SDS), and 1 mM EDTA at 65° C., followed by washing in 0.2×SSC/0.1% SDS at 42° C. (see Ausubel et al. (eds.), Current Protocols in Molecular Biology, Vol. 1, Green Publishing Associates, Inc., and John Wiley & Sons, Inc., N.Y. (1989), at p. 2.10.3). Also included in the present invention are polynucleotides that encode one or more of the CDR regions or the heavy and/or light chains of a monoclonal antibody of the present invention. General techniques for cloning and sequencing immunoglobulin variable domains and constant regions are well know. See, for example, Orlandi et al., *Proc. Nat'l Acad. Sci. USA* 86:3833 (1989).

The present invention also includes recombinant vectors including an isolated polynucleotide of the present invention. The vector can be, for example, in the form of a plasmid, a viral particle, or a phage. The appropriate DNA sequence can be inserted into a vector by a variety of procedures. In general, the DNA sequence is inserted into an appropriate restriction endonuclease site(s) in a vector by procedures known in the art. Such procedures are deemed to be within the scope of those skilled in the art. Large numbers of suitable vectors and promoters are known to those of skill in the art and are commercially available. The following vectors are provided by way of example. Bacterial vectors include, for example, pQE70, pQE60, pQE-9, pBS, pD10, phagescript, psiX174, pbluescript SK, pbsks, pNH8A, pNH16a, pNH18A, pNH46A, ptrc99a, pKK223-3, pKK233-3, pDR540, and pRIT5. Eukaryotic vectors include, for example, pWLNEO, pSV2CAT, pOG44, pXT1, pSG, pSVK3, pBPV, pMSG, and pSVL. However, any other plasmid or vector can be used.

The present invention also includes host cells containing the above-described vectors. The host cell can be a higher eukaryotic cell, such as a mammalian or insect cell, or a lower eukaryotic cell, such as a yeast cell. Or, the host cell can be a prokaryotic cell, such as a bacterial cell, or a plant cell. Introduction of a vector construct into the host cell can be affected by any suitable techniques, such as, for example, calcium phosphate transfection, DEAE-Dextran mediated transfection, or electroporation. (Davis, L., et al., Basic Methods in Molecular Biology, (1986)). A variety of cell lines may be used for expressing the antibody or functional part, including, but not limited to, mammalian cell lines. In one embodiment, the cell lines may be human. In another embodiment, bacterial or insect cell lines may be used. In one embodiment, the cell lines include Chinese hamster ovary (CHO) cells, variants of CHO cells (for example DG44), 293 cells and NSO cells. In another embodiment, cell lines include VERY, BHK, Hela, COS, MDCK, 293F, 293T, 3T3, W138, BT483, Hs578T, HTB2, BT2O and T47D, CRL7O3O and HsS78Bst cells.

Antibodies of the present invention can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

Also included in the present invention are phage display libraries expressing one or more hypervariable regions from a monoclonal antibody of the present invention, and clones obtained from such a phage display library. A phage display library is used to produce antibody derived molecules. Gene segments encoding the antigen-binding variable domains of antibodies are fused to genes encoding the coat protein of a bacteriophage. Bacteriophage containing such gene fusions are used to infect bacteria, and the resulting phage particles have coats that express the antibody-fusion protein, with the antigen-binding domain displayed on the outside of the bacteriophage. Phage display libraries can be prepared, for example, using the Ph.D.™-7 Phage Display Peptide Library Kit (Catalog #E8100S) or the Ph.D.™-12 Phage Display Peptide Library Kit (Catalog #E8110S) available from New England Biolabs Inc., Ipswich, MA. See, for example, Smith and Petrenko, *Chem Rev.* 1997; 97:391-410.

The present invention also includes in vitro and in vivo assays for the screening and identification of antibodies with endothelin receptor antagonist activity for use in the treatment of Alport syndrome. Such assays include, but are not limited to, any one of the various cell culture and animal model systems described herein. In vitro assays include, for example, cultured primary mesangial cells (for example, as described by Cosgrove et al., 2008, *Am J Pathol;* 172:761-773), cultured podocytes, and conditional immortalized glomerular epithelial cells (GEC's) (Rao et al., 2006, *Am J Pathol;* 169:32-46). The treatment (contacting) of such cultured cells with endothelin-1 induces the formation of drebrin-positive filopodial microspikes. Potential endothelin receptor antagonist activity of an agent may be identified and/or assayed by pretreatment (contacting) of the cells with the agent, with a potential endothelin receptor antagonist inhibiting, reducing and/or blocking the formation of microspikes in comparison to cells not pretreated with the agent. Any such assay may also include appropriate controls, including, but not limited to negative and/or positive controls.

The present invention includes methods of treating Alport syndrome in a subject by the administration of an anti-endothelin-1 antibody as described herein. The administration of such an antibody may, for example, inhibit migration of mesangial cells, inhibit irregular deposition of mesangial laminin 211 in the GBM, inhibit invasion of the capillary loops by mesangial cell processes, inhibit mesangial filopodial invasion of the glomerular capillary tuft, and/or prevent, or slow the onset of proteinuria.

The present invention includes methods of preventing, slowing, and/or managing glomerular disease progression in a subject diagnosed with Alport syndrome by the administration of an anti-endothelin-1 antibody as described herein.

The present invention includes methods of treating glomerulonephritis associated with Alport syndrome in a subject by administering an anti-endothelin-1 antibody as described herein.

The present invention includes methods of treating kidney injury due to biomechanical strain in Alport syndrome by administering an anti-endothelin-1 antibody as described herein.

The present invention includes methods of inhibiting deposition of laminin 211 in the glomerular basement membrane (GBM) by administering an anti-endothelin-1 antibody as described herein. The laminins are major proteins in the basal lamina, a layer of the basement membrane, a protein network foundation for most cells and organs. Laminins are heterotrimeric proteins that contain an $\alpha$-chain, a $\beta$-chain, and a $\gamma$-chain, found in five, four, and three genetic variants, respectively. The laminin molecules are named according to their chain composition. Thus, laminin-511 contains $\alpha 5$, $\beta 1$, and $\gamma 1$ chains (Aumailley et al., 2005, *Matrix Biol;* 24(5):326-32). Fourteen other chain combinations have been identified in vivo. Laminin-211 (composed of $\alpha 2$, $\beta 1$ and $\gamma 1$ chains (Ehrig et al., 1991, *PNAS;* 87:3264-3268) is the main laminin isoform in skeletal muscle (Leivo and Engvall, 1988, *PNAS;* 85:1544-1588; and Patton, 1997, *J Cell Biol;* 139:1507-1521) and identification of laminin $\alpha 2$ chain mutations in a severe form of congenital muscular dystrophy (merosin-deficient congenital muscular dystrophy; MDC1A) established the importance of laminin-211 for normal muscle function (Helbling-Leclerc et al., 1995, *Nat Genet;* 11:216-218).

The present invention includes methods of inhibiting mesangial cell process invasion of the glomerular capillary loop of the kidney by administering an anti-endothelin-1 antibody as described herein.

The present invention includes methods of preventing, slowing, managing, and/or treating the one or more of the sensory and/or hearing losses associated with Alport syndrome by administering an anti-endothelin-1 antibody as described herein.

The present invention includes methods of preventing, slowing, managing, and/or treating pulmonary hypertension in a subject by administering an anti-endothelin-1 antibody as described herein.

The present invention includes methods of preventing, slowing, managing, and/or treating kidney diseases associated with endothelin-1 induced pathogenesis, including, but not limited to lowering blood pressure in the glomerular tuft, and preventing, slowing, managing, and/or treating diabetic kidney nephropathy, in a subject by administering an anti-endothelin-1 antibody as described herein.

The present invention includes methods of preventing, slowing, managing, and/or treating endothelin-1 induced pathogenesis in a subject by administering an anti-endothelin-1 antibody as described herein.

The present invention includes methods of treating kidney injury due to biomechanical strain in Alport syndrome by administering an anti-endothelin-1 antibody as described herein.

In some applications, the methods of the present invention may be used for the presymptomatic treatment of individuals, with the administration of an anti-endothelin-1 antibody as described herein beginning after the determination or diagnosis of Alport syndrome, prior to the onset of symptoms, such as for, example, proteinuria. The diagnosis of Alport syndrome in an individual may be made, for example, by family medical history, genetic testing, immunodiagnostic skin biopsy testing, and/or molecular diagnostic marker testing. Methods of the present invention may also include one or more steps of obtaining a diagnosis of Alport syndrome by the use of one or more such diagnostic means.

With the method of the present invention, one or more additional therapeutic modalities may be administered along with one or more antibodies of the present disclosure. In some aspects of the present invention, the administration of an antibody of the present disclosure may allow for the effectiveness of a lower dosage of other therapeutic modalities when compared to the administration of the other therapeutic modalities alone, providing relief from the toxicity observed with the administration of higher doses of the other modalities. One or more additional therapeutic agents may be administered before, after, and/or coincident to the administration of an antibody of the present disclosure. Antibodies of the present disclosure and additional therapeutic agents may be administered separately or as part of a mixture of cocktail. As used herein, an additional therapeutic agent may include, for example, an agent whose use for the treatment of Alport syndrome, kidney disease, kidney failure, and/or proteinuria is known to the skilled artisan. For example, an angiotensin-converting enzyme (ACE) inhibitor, such as ramipril or analapril, may be administered. For example, a small molecule endothelin receptor antagonist, such as bosentan, sitaxsentan, ambrisentan, macitentan, sparsentan, and/or altrasentan, may be administered.

As used herein "treating" or "treatment" can include therapeutic and/or prophylactic treatments. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis.

The antibodies of the present disclosure can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical, or injection. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intraperitoneal, and intratumoral administration. In this connection, sterile aqueous media that can be employed will be known to those of skill in the art. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA. Such preparation may be pyrogen-free.

The present invention includes compositions of one or more of the antibodies described herein. A composition may also include, for example, buffering agents to help to maintain the pH in an acceptable range or preservatives to retard microbial growth. Such compositions may also include a pharmaceutically acceptable carrier. As used herein, the term "pharmaceutically acceptable carrier" refers to one or more compatible solid or liquid filler, diluents or encapsulating substances which are suitable for administration to a human or other vertebrate animal. The compositions of the present disclosure are formulated in pharmaceutical preparations in a variety of forms adapted to the chosen route of administration.

Therapeutically effective concentrations and amounts may be determined for each application herein empirically by testing the compounds in known in vitro and in vivo systems, such as those described herein, dosages for humans or other animals may then be extrapolated therefrom. With the methods of the present disclosure, the efficacy of the administration of one or more agents may be assessed by any of a variety of parameters known in the art.

It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

An antibody of the present disclosure may be administered at once or may be divided into a number of smaller doses to be administered at intervals of time. For example, an agent of the present disclosure may be administered twice a day, three times a day, four times a day, or more. For example, an agent of the present disclosure may be administered every other day, every third day, once a week, every two weeks, or once a month. In some applications, an agent of the present disclosure may be administered continuously, for example by a controlled release formulation or a pump. In some applications, administration on antibody of the present disclosure may be at a dosage similar to the accepted dosage for other therapeutic antibodies.

It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

In some applications, administration on antibody of the present disclosure may be short term or long term. In some aspects, long term administration may be for weeks, months, years, or decades.

In some therapeutic embodiments, an "effective amount" of an agent is an amount that results in a reduction of at least one pathological parameter. Thus, for example, in some aspects of the present disclosure, an effective amount is an amount that is effective to achieve a reduction of at least about 10%, at least about 15%, at least about 20%, or at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, compared to the expected reduction in the parameter in an individual not treated with the agent.

As used herein, the term "subject" includes, but is not limited to, humans and non-human vertebrates. In preferred embodiments, a subject is a mammal, particularly a human. A subject may be an "individual," "patient," or "host." In some aspects, a subject is an individual diagnosed with Alport syndrome. Diagnosis may be by any of a variety of means, including, but not limited to, family history, clinical presentation, pathological determination, and/or genetic testing. Such as subject may be a male or a female. Non-human vertebrates include livestock animals, companion animals, and laboratory animals. Non-human subjects also include non-human primates as well as rodents, such as, but not limited to, a rat or a mouse. Non-human subjects also include, without limitation, chickens, horses, cows, pigs, goats, dogs, cats, guinea pigs, hamsters, mink, and rabbits.

As used herein "in vitro" is in cell culture and "in vivo" is within the body of a subject.

As used herein, "isolated" refers to material that has been either removed from its natural environment (e.g., the natural environment if it is naturally occurring), produced using recombinant techniques, or chemically or enzymatically synthesized, and thus is altered "by the hand of man" from its natural state.

All headings are for the convenience of the reader and should not be used to limit the meaning of the text that follows the heading, unless so specified.

The invention is defined in the claims. However, below is provided a non-exhaustive list of non-limiting embodiments. Any one or more of the features of these embodiments may be combined with any one or more features of another example, embodiment, or aspect described herein.

1. One embodiment includes an antibody or antigen binding fragment thereof capable of specifically binding human endothelin-1, the antibody or antigen binding fragment thereof comprising a heavy chain complementarity determining region (CDR) 1, a heavy chain variable region CDR2, a heavy chain variable region CDR3, a light chain variable region CDR1, a light chain variable region CDR2, and a light chain variable region CDR3 of the monoclonal antibody produced by the hybridoma cell line Nab #15 7D 489 deposited under ATCC[[®]] Patent Deposit Designation PTA-125817.

2. One embodiment includes an antibody or antigen binding fragment thereof capable of specifically binding human endothelin-1, the antibody or antigen binding fragment thereof comprising a heavy chain complementarity determining region (CDR) 1, a heavy chain variable region CDR2, a heavy chain variable region CDR3, a light chain variable region CDR1, a light chain variable region CDR2, and a light chain variable region CDR3 of the monoclonal antibody produced by the hybridoma cell line Nab #7 3G 9A4 deposited under ATCC[[®]] Patent Deposit Designation PTA-125818.

3. One embodiment includes an antibody or antigen binding fragment thereof capable of specifically binding human endothelin-1, the antibody or antigen binding fragment thereof comprising a heavy chain complementarity determining region (CDR) 1, a heavy chain variable region CDR2, a heavy chain variable region CDR3, a light chain variable region CDR1, a light chain variable region CDR2, and a light chain variable region CDR3 of the monoclonal antibody produced by the hybridoma cell line Nab #1 5D 1087 deposited under ATCC[[®]] Patent Deposit Designation PTA-125819.

4. One embodiment includes an antibody or antigen binding fragment thereof capable of specifically binding human endothelin-1, the antibody or antigen binding fragment thereof comprising the heavy chain variable region (VH) and light chain variable region (VL) of the monoclonal antibody produced by the hybridoma cell line Nab #15 7D 489 deposited under ATCC[[®]] Patent Deposit Designation PTA-125817.

5. One embodiment includes an antibody or antigen binding fragment thereof capable of specifically binding human endothelin-1, the antibody or antigen binding fragment thereof comprising the heavy chain variable region (VH) and light chain variable region (VL) of the monoclonal antibody produced by the hybridoma cell line Nab #7 3G 9A4 deposited under ATCC[[®]] Patent Deposit Designation PTA-125818.

6. One embodiment includes an antibody or antigen binding fragment thereof capable of specifically binding human endothelin-1, the antibody or antigen binding fragment thereof comprising the heavy chain variable region (VH) and light chain variable region (VL) of the monoclonal antibody produced by the hybridoma cell line Nab #1 5D 1087 deposited under ATCC[[®]] Patent Deposit Designation PTA-125819.

7. One embodiment includes the monoclonal antibody produced by hybridoma cell line Nab #15 7D 489 deposited under ATCC[[®]] Patent Deposit Designation PTA-125817, or an antigen binding fragment thereof.

8. One embodiment includes the monoclonal antibody produced by hybridoma cell line Nab #7 3G 9A4 deposited under ATCC[[®]] Patent Deposit Designation PTA-125818, or an antigen binding fragment thereof.

9. One embodiment includes the monoclonal antibody produced by hybridoma cell line Nab #1 5D 1087 deposited under ATCC[[®]] Patent Deposit Designation PTA-125819, or an antigen binding fragment thereof.

10. Also included are antigen binding fragment thereof of any one of embodiments 1 to 9, wherein the antigen binding fragment thereof is selected from the group consisting of a Fab fragment, a Fab' fragment, a $F(ab)_2$ fragment, a Fv fragment, and a single chain variable fragment (scFv).

11. Also included are an antibody or antigen binding fragment thereof of any one of embodiments 1 to 10, wherein the antibody or a functional part thereof is fully human, humanized, or chimeric.

12. Also included are an antibody or antigen binding fragment thereof of any one of embodiments 1 to 11, comprising a human IgG1 isotype.

13. Also included are an antibody or antigen binding fragment thereof of any one of embodiments 1 to 12, comprising an Fc region comprising tyrosine (Y) at amino acid position 252, threonine (T) at amino acid position 254, and glutamic acid (E) at amino acid position 256, wherein the numbering corresponds to the EU index in Kabat.

14. Also included are an antibody or antigen binding fragment thereof of any one of embodiments 1 to 13, wherein the antibody neutralizes the activity of human endothelin-1.

15. Also included are an antibody or antigen binding fragment thereof of any one of embodiments 1 to 14, wherein the antibody or antigen binding fragment thereof inhibits the formation of drebrin-positive filopodial microspikes in cultured mesangial cells contacted with endothelin-1.

16. Also included are an antibody or antigen binding fragment thereof of any one of embodiments 1 to 15, wherein the antibody or antigen binding fragment thereof inhibits the polymerization of globular actin (G-actin) to filamentous actin (F-actin) in cultured mesangial cells contacted with endothelin-1.

17. Also included are a composition comprising the antibody or antigen binding fragment thereof of any one of embodiments 1 to 16.

18. Also included are a kit comprising the monoclonal antibody or antigen binding fragment thereof of any one of embodiments 1 to 16 or compositions of embodiment 17.

19. One embodiment includes the Nab #15 7D 489 hybridoma cell line as deposited under ATCC[[®]] Patent Deposit Designation PTA-125817, and progeny thereof.

20. One embodiment includes the Nab #7 3G 9A4 hybridoma cell line as deposited under ATCC[[®]] Patent Deposit Designation PTA-125818, and progeny thereof.

21. One embodiment includes the Nab #1 5D 1087 hybridoma cell line as deposited under ATCC[[®]] Patent Deposit Designation PTA-125819, and progeny thereof.

22. Also included are a method of treating Alport syndrome in a subject, the method comprising administering an effective amount of an antibody or antigen binding fragment thereof of any one of embodiments 1 to 16 or a composition of embodiment 17 to the subject.

23. Also included are a method of preventing glomerular disease progression in a subject diagnosed with Alport syndrome, the method comprising administering an effective amount of an antibody or antigen binding fragment thereof of any one of embodiments 1 to 16 or a composition of embodiment 17 to the subject.

24. Also included are a method of treating glomerulonephritis in a subject, the method comprising administering an effective amount of an antibody or antigen binding fragment thereof of any one of embodiments 1 to 16 or a composition of embodiment 17 to the subject.

25. Also included are a method of treating kidney injury due to biomechanical strain in Alport syndrome, the method comprising administering an effective amount of an antibody or antigen binding fragment part thereof of any one of embodiments 1 to 16 or a composition of embodiment 17 to the subject.

26. Also included are a method of inhibiting deposition of laminin 211 in the glomerular basement membrane (GBM) in a subject, the method comprising administering an effective amount of an antibody or antigen binding fragment thereof of any one of embodiments 1 to 16 or a composition of embodiment 17 to the subject.

27. Also included are a method of inhibiting mesangial cell process invasion of the glomerular capillary loop in a kidney of a subject, the method comprising administering an effective amount of an antibody or antigen binding fragment thereof of any one of embodiments 1 to 16 or a composition of embodiment 17 to the subject.

28. Also included are a method of inhibiting Alport glomerular pathogenesis in a subject; the method comprising:

determining that the subject is at risk for developing Alport glomerular disease; and administering an effective amount of an antibody or antigen binding fragment thereof of any one of embodiments 1 to 16 or a composition of embodiment 17 to the subject.

29. In some aspects of embodiment 28, wherein the determination that the subject is at risk for developing Alport glomerular disease is determined by family medical history, genetic testing, immunodiagnostic skin biopsy testing, and/or molecular diagnostic marker testing.

30. In some aspects of a method of any one of embodiments 22 to 29, one or more sensory and/or hearing losses associated with Alport syndrome is treated or prevented.

31. Also included is a method of treating pulmonary hypertension in a subject, the method comprising administering an effective amount of an antibody or antigen binding fragment thereof of any one of embodiments 1 to 16 or a composition of embodiment 17 to the subject.

32. Also included is a method of treating a kidney disease associated with endothelin-1 induced pathogenesis in a subject, the method comprising administering an effective amount of an antibody or antigen binding fragment thereof of any one of embodiments 1 to 16 or a composition of embodiment 17 to the subject.

33. Also included is a method of treating diabetic kidney nephropathy in a subject, the method comprising administering an effective amount of an antibody or antigen binding fragment thereof of any one of embodiments 1 to 16 or a composition of embodiment 17 to the subject.

34. Also included is a method of inhibiting endothelin-1 induced pathogenesis in a subject, the method comprising administering an effective amount of an antibody or antigen binding fragment thereof of any one of embodiments 1 to 16 or a composition of embodiment 17 to the subject.

35. In some aspects of a method of any one of embodiments 22 to 34, the method further comprises administering an angiotensin-converting enzyme (ACE) inhibitor.

36. In some aspects of a method of embodiments 35, the ACE inhibitor is selected from ramipril and/or analapril.

37. In some aspects of a method of any one of embodiments 22 to 36, the methods further comprises administering an endothelin receptor antagonist.

38. In some aspects of a method of embodiment 37, the endothelin receptor antagonist is selected from bosentan, sitaxsentan, ambrisentan, macitentan, sparsentan, and/or altrasentan.

39. A further embodiment includes an isolated nucleic acid sequence encoding the antibody or antigen binding fragment thereof of any one of embodiments 1 to 16.

40. A further embodiment includes an isolated polynucleotide sequence comprising the nucleic acid sequence coding for the heavy chain, the light chain, the heavy chain variable region, the light chain variable region, or one or more complementarity determining regions of the antibody or antigen binding fragment thereof of any one of embodiments 1 to 16.

41. A further embodiment includes an expression vector comprising the isolated polynucleotide of embodiment 39 or 40.

42. A further embodiment includes a method of producing a substantially purified antibody, or antigen binding fragment thereof, the method comprising expressing the isolated nucleotide sequence of any one of embodiments 39 or 40 or the expression vector of embodiment 41 and harvesting the expressed antibody, or antigen binding fragment thereof.

43. A further embodiment includes a host cell comprising the expression vector of embodiment 41.

44. A further embodiment includes a method of producing a substantially purified antibody, or antigen binding fragment thereof, the method comprising growing a host cell of embodiment 43 under conditions in which the antibody, or antigen binding fragment thereof, is expressed and harvesting the expressed antibody, or antigen binding fragment thereof.

The present invention is illustrated by the following examples. It is to be understood that the particular examples, materials, amounts, and procedures are to be interpreted broadly in accordance with the scope and spirit of the invention as set forth herein.

EXAMPLES

Example 1

Alport syndrome (incidence about 1 in 5000) is characterized by delayed onset progressive glomerulonephritis associated with sensorineural hearing loss and retinal flecks (Kashtan and Michael, 1996, *Kidney Int;* 50(5):1445-1463). The most common form (80%) is X-linked and caused by mutations in the type IV collagen COL4A5 gene (Barker et al., 1990, *Science;* 248(4960):1224-7). The two autosomal forms of the disease account for the remaining 20% of Alport patients and result from mutations in the COL4A3 and COL4A4 genes (Mochizuki et al., 1994, *Nat Genet;* 8(1):77-81). The α3(IV), α4(IV) and α5(IV) proteins form a heterotrimer and are assembled into a subepithelial network in the mature glomerular basement membrane that is physically and biochemically distinct from a subendothelial type IV collagen network comprised of α1(IV) and α2(IV) heterotrimers (Kleppel et al., 1992, *J Biol Chem;* 267(6): 4137-4142). Mutation in any one of the three type IV collagen genes that cause Alport syndrome results in the absence of all three proteins in the glomerular basement membrane (GBM) due to an obligatory association in basement membrane collagen assembly to form functional heterotrimers (Kalluri and Cosgrove, 2000, *J Biol Chem;* 275(17):12719-12724). Thus, the net result for all genetic forms of Alport syndrome is the absence of the α3(IV) α4(IV) α5(IV) subepithelial collagen network, resulting in a thinner GBM type IV collagen network comprised only of α1(IV) and α2(IV) heterotrimers.

This change in basement membrane composition does not result in immediate pathology. The GBM appears to function adequately for the first few years of life and sometimes past the first decade (Kashtan et al., 1998, *Pediatr Nephrol;* 12(4):269-27). This delayed onset predicts a triggering mechanism for glomerular disease initiation and a theoretical window for therapeutic intervention that may arrest or significantly ameliorate Alport renal disease in its earliest stages. The activation of genes encoding GBM matrix molecules, matrix metalloproteinases (MMPs), and pro-inflammatory cytokines have all been linked to the progression of Alport glomerular disease. These, however, are events that occur after the onset of proteinuria, and are therefore likely downstream of disease initiation events (Sayers et al., 1999, *Kidney Int;* 56(5):1662-1673; Cosgrove et al., 2000, *Am J Pathol;* 157(5):1649-59; Rao et al., 2006, *Am J Pathol;* 169(1):32-46; Zeisberg et al., 2006, *PLoS Medicine;* 3(4), e100; and Cosgrove et al., 2008, *Am J Pathol;* 172(3):761-7737-11).

Consistent with this notion, experiments aimed at blocking these pathways have offered only limited therapeutic benefit in mouse models for Alport syndrome (Cosgrove et al., 2000, *Am J Pathol;* 157(5):1649-59; Rao et al., 2006, *Am J Pathol;* 169:32-46; Zeisberg et al., 2006, *PLoS Medicine;* 3(4), e100; Koepke et al., 2007, *Nephrol Dial Transplant;* 22(4):1062-9). One of the earliest events documented is the appearance of an irregular deposition of laminin 211 in the GBM of Alport mice (Cosgrove et al., 2000, *Am J Pathol;* 157(5):1649-59), an observation confirmed in both Alport dogs and human patients with the disease (Kashtan et al., 2001, *J Am Soc Nephrol;* 12:252-60). This laminin is normally found only in the mesangium of the glomerulus and is not expressed in the GBM at any stage of embryonic development (Miner et al., 1997, *J Cell Biol;* 137(3):685-701). Indeed, several other mesangial matrix proteins appear in the GBM of Alport mice, including laminin 111 and fibronectin (Cosgrove et al., 2008, *Am J Pathol;* 172(3):761-7737-11; and St. John and Abrahamson, 2001, *Kidney Int;* 60(3):1037-1046).

Since the α1(IV)/α2(IV) collagen network contains significantly fewer interchain disulfide crosslinks (Gunwar et al., 1998, *J Biol Chem;* 273(15):8767-75), and since the Alport GBM is thinner than normal (Kamenetsky et al., 2010, *J Digital Imaging;* 23:463-474), the Alport GBM is likely to be more elastic than mature wild type GBM, resulting in elevated biomechanical strain on the glomerular cells at their points of contact with the GBM. Consistent with this, glomeruli from pre-proteinuric Alport mice have been shown to have elevated deformability relative to wild type glomeruli (Wyss et al., 2011, *Am J Physiol Cell Physiol;* 300:C397-C405), and salt-induced hypertension has been shown to accelerate glomerular disease progression in Alport mice (Meehan et al., 2009, *Kidney Int;* 76:968-976), suggesting strain-mediated responses can drive glomerular pathology.

The cellular origin of GBM laminin 211 has not been previously determined. It has recently been shown that the source of GBM laminin 211 in Alport GBM is mesangial cell processes, which are invading the capillary tufts (Zallocchi et al., 2013, *Am J Pathol;* 183(4):1269-80). Salt-mediated hypertension exacerbates this mesangial process invasion. Also shown was that deposition of laminin 211 in the GBM activates focal adhesion kinase in podocytes, which leads to NF-kappaB activation and induction of pro-inflammatory cytokines as well as MMPs, driving the progression of Alport glomerular disease (Delimont et al., *PLoS One,* 2014 Jun. 10; 9(6)). A knockout mouse for the integrin α3β1 co-receptor CD151, which results in reduced adhesion of podocytes pedicles to GBM laminin 521, also develops mesangial process invasion of the capillary loops with GBM deposition of laminin 211, demonstrating the same phenotype for a completely unrelated molecular component of the glomerular capillary structural barrier (Zallocchi et al., 2013, *Am J Pathol;* 183(4):1269-80). The CD151 knockout mouse model also shows accelerated glomerular disease progression in response to hypertension (Sachs et al., 2012, *J Clin Invest;* 122(1):348-58). The biomechanical stretching of cultured mesangial cells induces pro-migratory cytokines TGF-β1 and CTGF, both known to be induced in Alport glomeruli (Sayers et al., 1999, *Kidney Int;* 56(5):1662-1673; and Koepke et al., 2007, *Nephrol Dial Transplant;* 22(4):1062-9).

Using inhibitor studies, it was demonstrated that mesangial cell migration is mediated by the Rho GTPase RAC1 and that treatment of Alport mice with a RAC1 inhibitor blocks mesangial process invasion of the glomerular capillary tufts, implicating the activation of Rac1 in this process (Zallocchi et al., 2013, *Am J Pathol;* 183(4):1269-80). These data have defined a role for biomechanical strain mediated induction of mesangial cell filopodial invasion as a key aspect of Alport glomerular disease initiation and set the stage for defining novel therapeutic targets aimed at blocking this process. Endothelin 1 is induced in the endothelial cells of Alport mice before the onset of proteinuria, and that expression is further induced by hypertension ((Dufek et al., 2016, *Kidney Int;* 90(2):300-310). It has been previously shown that endothelin 1 activates CDC42/RAC1 in glomerular mesangial cells via activation of endothelin receptors (Chahdi et al., 2005, *J Biol Chem;* 280(1):578-84; and Chahdi and Sorokin, 2006, *Exp Biol Med (Maywood);* 231(6):761-5)), and it is well established that biomechanical stretching induces endothelin 1 expression and secretion by endothelial cells (Babu et al., 2012, *Sci Signal;* 5(254):ra91). It has also been shown that ET-1 treatment of primary cultured mesangial cells activates CDC42 and induces the formation of drebrin-positive actin microspikes, consistent with the activation of filopodia (Zallocchi et al., 2013, *Am J Pathol;* 183(4):1269-80).

With this example, this assay has now been adapted as a reliable bioassay for screening drugs capable of neutralizing the activation step. This bioassay was employed to rapidly screen anti-ET-1 monoclonal antibodies for function-neutralizing activity. Four anti-ET-1 monoclonal antibodies have been identified that show neutralizing activity. These antibodies are thus drug candidates and will be screened as discussed below. These four monoclonal antibodies have been ranked by biochemical analysis and Biacore two are selected for full development.

While the presence of abnormal laminins in the Alport GBM was described 15 years ago (Cosgrove et al., 2000, *Am J Pathol;* 157(5):1649-59; and Kashtan et al., 2001, *J Am Soc Nephrol;* 12:252-60), the functional significance of this observation has, until recently, remained unknown. Recently, FAK activation in podocyte foot processes has been observed, specifically in regions of the GBM where abnormal laminin deposition is occurring (Delimont et al., *PLoS One,* 2014 Jun. 10; 9(6)). This is observed as early as P10, long before detectable proteinuria for autosomal Alport mice on the 129 Sv background (about 3 weeks). The cellular source of GBM laminin 211 is mesangial filopodia. If this formation of filopodia is blocked by way of a small molecule inhibitor for RAC1/CDC42 Rho GTPases, laminin 211 deposition in the Alport GBM is largely blocked (Zallocchi et al., 2013, *Am J Pathol;* 183(4):1269-80). Similarly, when endothelin A receptors in Alport mice are blocked with the small molecule inhibitor Sitaxentan, markedly reduced mesangial process invasion of the glomerular capillaries is observed, as well as delayed the onset and progression of proteinuria, ameliorated GBM structural abnormalities, and significantly reduced glomerular expression of MMPs and pro-inflammatory cytokines. Collectively, these studies define a molecular mechanism that is key to the initiation of glomerular pathology in Alport syndrome. This mechanism has been recently confirmed in a dog model for Alport syndrome (Clark et al., 2016, *PLoS One;* 11(12):e0168343).

Figure 1:
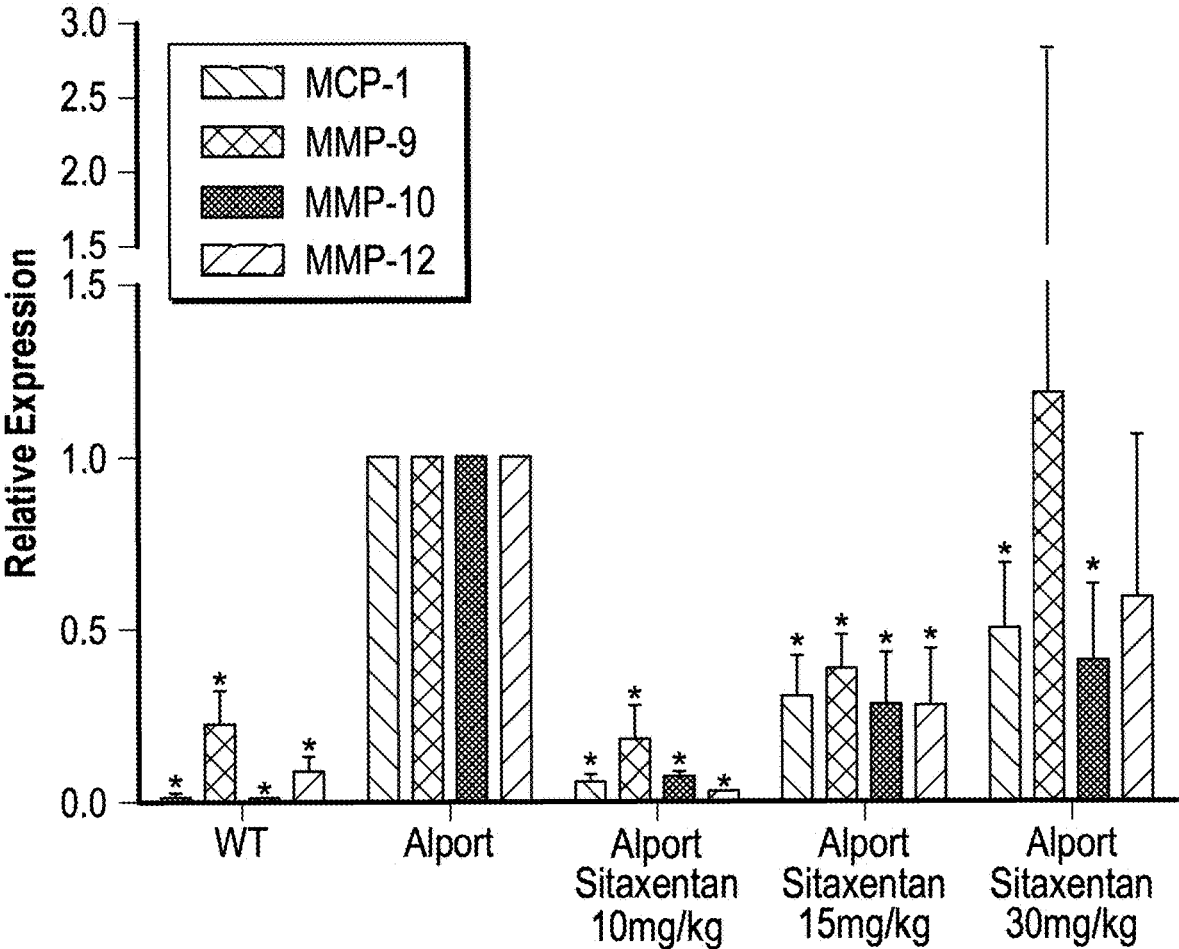
FIG. 1. Higher doses of Sitaxentan are renotoxic. Alport mice were treated with the indicated dose of Sitaxentan once daily from 2 to 7 weeks of age. Real time RT-PCR analysis for the indicated transcripts was performed on glomerular RNA. Higher levels of these transcripts are associated with glomerular pathology. At the 30 mg/kg dose, proteinuria, BUN, fibrosis scores, and glomerulosclerosis scores were not statistically different from vehicle treated Alport mice.

This combined with data demonstrating mesangial processes in the GBM of human Alport glomeruli (Zallocchi et al., 2013, *Am J Pathol;* 183(4):1269-80), establish that this mechanism is not specific to the mouse model. Sitxentan, Opsumit, Letairus, and Bosentan are all related compounds that block endothelin receptor activation and are (or have been) approved for treating pulmonary hypertension. They are notoriously toxic with significant off target effects that preclude their use for the treatment of chronic kidney disease, especially in children. As shown in FIG. 1, while a low dose (10 mg/kg) of Sitaxentan ameliorated Alport pathogenesis, increasing doses of Sitaxentan exacerbated renal disease, indicative of toxicity. A dose of 5 mg/kg had little to no significant therapeutic effect. Therefore, it is likely that the renoprotective effect observed at 10 mg/kg has some level of toxicity when chronically administered, which likely accounts for the nominal 20% increase in lifespan observed in the Sitaxentan study ((Dufek et al., 2016, *Kidney Int;* 90(2):300-310).

Neutralizing antibodies versus small molecule inhibitors: Biologics accounted for 17% of top 100 pharmaceutical sales in 2004 and that has risen to over 40% in 2016. The reason for this is many fold. They can interact with challenging targets, like the small globular ET-1 peptide. They have a better economic return than small molecules with a much higher likelihood of making it into the clinical marketplace. These properties incentivize investment for pre-clinically promising mAbs. Their high target specificity reduces the likelihood for drug/drug interactions (for example our abs with ACE or ARB inhibitors). Small molecules have a clear advantage in that they can be designed as ligands that can interact with ion channels, receptors, and the catalytic cavities of enzymes. There are negative side effects for both small molecules and neutralizing antibodies (nAbs). For the antibodies, the most common is the development of allergic reactions, which can be largely limited by modern humanization techniques. Several other much more severe (and even fatal) side effects have been encountered, that are summarized in by Hansel et al. (Hansel et al., 2010, *Nat Rev Drug Discov;* 9(4):325-38). It is difficult to know whether such effects (some mechanistically driven) will be encountered, however the fact that deletion of ET-1 in mice had no effect on health suggests that neutralization of its activity will likely be relatively safe (Kisanuki et al., 2010, *Hypertension;* 56(1):121-8). Disadvantages of small molecules are many. They are unnatural formulations that often have off target effects as well as mechanism driven toxicities that make their fail rate much higher than that for biologics. Engaging a receptor with a small molecule may have the desired PD outcome that comes with unwanted disruptions in homeostasis, such as the effects shown in FIG. 2 for Sitaxentan and Ambrisentan in the renal glomerulus.

Glomerular RNA from sitaxentan-treated and neutralizing antibody-treated mice was analyzed using QIAGEN mouse fibrosis microarrays. Surprisingly, Sitaxentan was markedly inducing a number of pro-inflammatory cytokines and regulatory molecules, including the well-studied Snail1 transcription factor that has previously been linked to renal fibrosis (Grande et al., 2015, *Nat Med;* 21(9):989-97). Similar results were obtained with Ambrisentan. This suggests that engagement of $ET_AR$ by Sitaxentan or Ambrisentan has effects that might directly damage the Alport kidney. When glomerular RNA from nAb #7-treated mice was analyzed, elevated expression of these genes was not observed (FIG. 2), providing direct evidence implicating an advantage of the nAb therapy over that of the small molecule approach.

FIG. 15 shows an overview of mechanism for Alport glomerular disease initiation. The changes in GBM composition result in elevated biomechanical strain on all glomerular cells. In the endothelial cells, this results in elevated expression of endothelin-1, which activates the endothelin A receptors on mesangial cells. $ET_AR$ signaling in mesangial cells results in the activation of the small GTPase CDC42 which induces the formation of filopodia (shown in red) at the mesangial angles. These filopodia invade the sub-endothelial aspect of the GBM and deposit mesangial proteins in the GBM, including laminin α2 (shown in green). Laminin α2 activates focal adhesion kinase (*FAK) in the podocyte pedicles, which in turn activates NFkappaB, resulting in nuclear translocation and activation of pro-inflammatory genes (from Cosgrove and Liu, 2017, *Matrix Biol;* 57-58: 45-54).

The rigor of prior research is based largely on published data demonstrating the importance of strain-mediated induction of ET-1 in activating a pro-inflammatory pathway in podocytes via activation of mesangial filopodial invasion of the glomerular capillaries. The filopodia deposit mesangial proteins, activating FAK and downstream NFkappaB in podocytes, resulting in gene dysregulation that promote GBM destruction and glomerulosclerosis (Mechan et al., 2009, *Kidney Int;* 76:968-976; Zallocchi et al., 2013, *Am J Pathol;* 183(4):1269-80; Delimont et al., *PLoS One,* 2014 Jun. 10; 9(6); and Dufek et al., 2016, *Kidney Int;* 90(2):300-31). In addition, Endothelial cell-specific deletion of the EDN1 gene in mice does not affect development or lifespan (Kisanuki et al., 2010, *Hypertension;* 56(1):121-8), supporting the idea that neutralization of ET-1 activity will be relatively safe. One significant weakness of this prior work is that $ET_AR$ inhibition only marginally increased lifespan, suggesting mechanism-based toxicity or off target effects were limiting the degree of renoprotection. This assumption is supported by FIG. 1 and FIG. 2, which suggests ET-1 neutralization might offer a superior approach mechanistically. Thus, the identification and qualification of ET-1 neutralizing antibodies has the potential to delay the onset and progression of Alport glomerular disease. Since the mechanism of action is distinct from ACE inhibition, this biologic has strong potential to synergize with the current standard of care for these patients.

Research Design and Methods:

As previously reported, hypertension accelerated the progression of Alport glomerular disease, suggesting a key role for biomechanical strain in the disease mechanism (Meehan et al., 2009, *Kidney Int;* 76:968-976). Based on the data demonstrating the induction of mesangial process invasion of the glomerular capillaries, whether biomechanical stretching of the capillary tuft activates actin cytoskeletal dynamics in Alport glomeruli was investigated. This observation was extended with the discovery that mesangial processes invade the glomerular capillaries in a biomechanical strain-mediated Rac1/CDC42-activation mechanism (Zallocchi et al., 2013, *Am J Pathol;* 183(4):1269-80).

Importantly, the mesangial filopodia are depositing mesangial matrix proteins, including laminin 211, which activates focal adhesion kinase in glomerular podocytes, resulting in the activation of genes encoding pro-inflammatory cytokines and metalloproteinases, which drive the progression of GBM damage (Delimont et al., *PLoS One,* 2014 Jun. 10; 9(6)). The following provides background plus examples of the assays that will be used to qualify pharmacodynamic efficacy of the function neutralizing antibodies. This pre-clinical data will support the use of these biological therapeutics as candidates for human clinical trials.

Figures 3A, 3B:
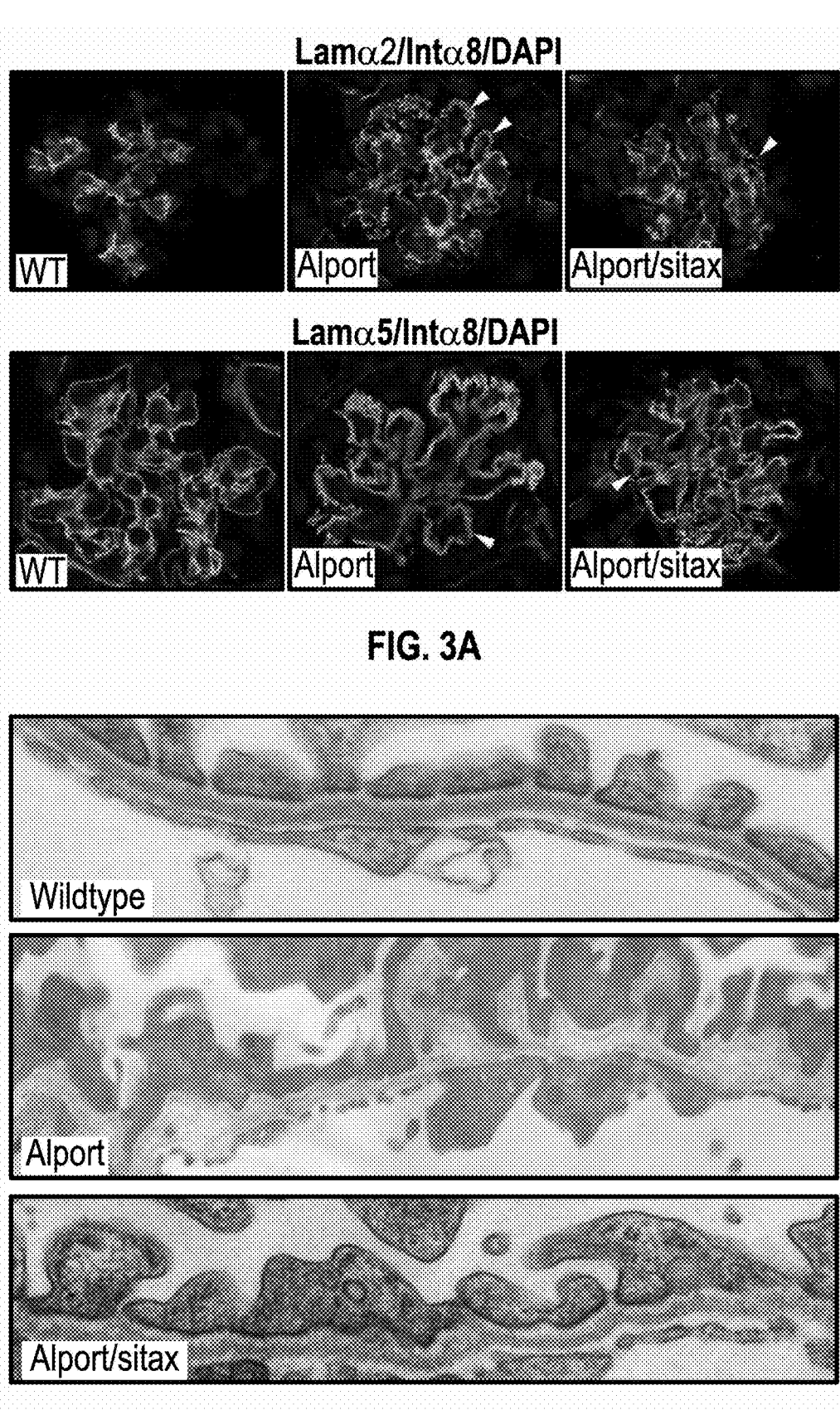
FIGS. 3A and 3B. Endothelin A receptor blockade prevents mesangial process invasion of glomerular capillaries and ameliorates GBM damage. 129-Alport animals were treated with the endothelin A receptor specific blocking agent Sitaxentan from 2 weeks to 7 weeks of age.
Figure 4A:
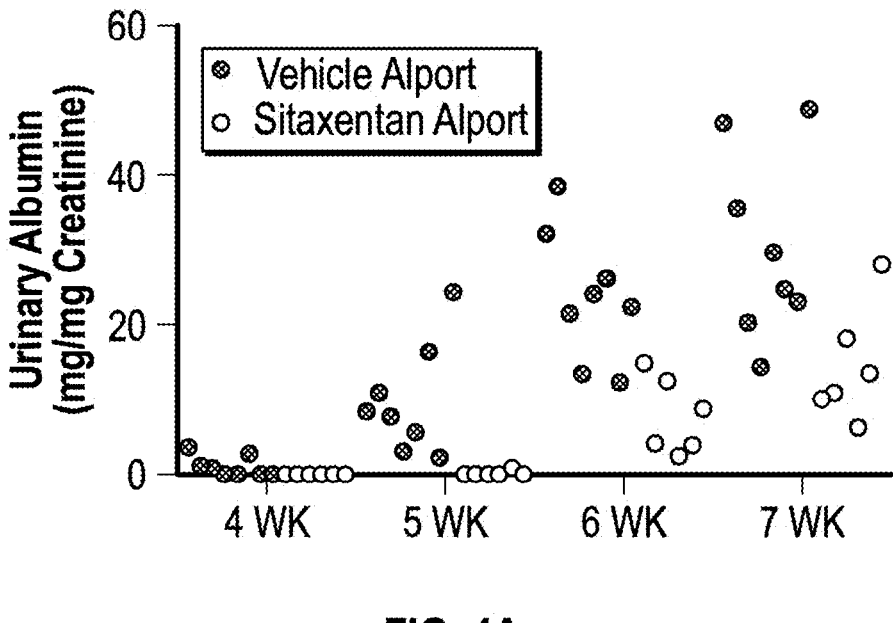
FIGS. 4A and 4B. Sitaxentan treatment of Alport mice significantly delays the onset and progression of proteinuria and reduces serum BUN levels.
Figure 4B:
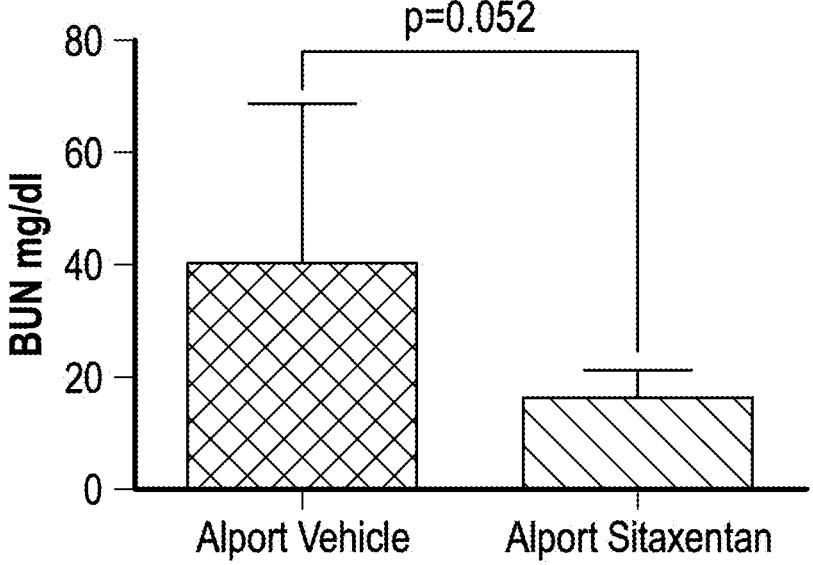
Figures 5A, 5B, 5C:
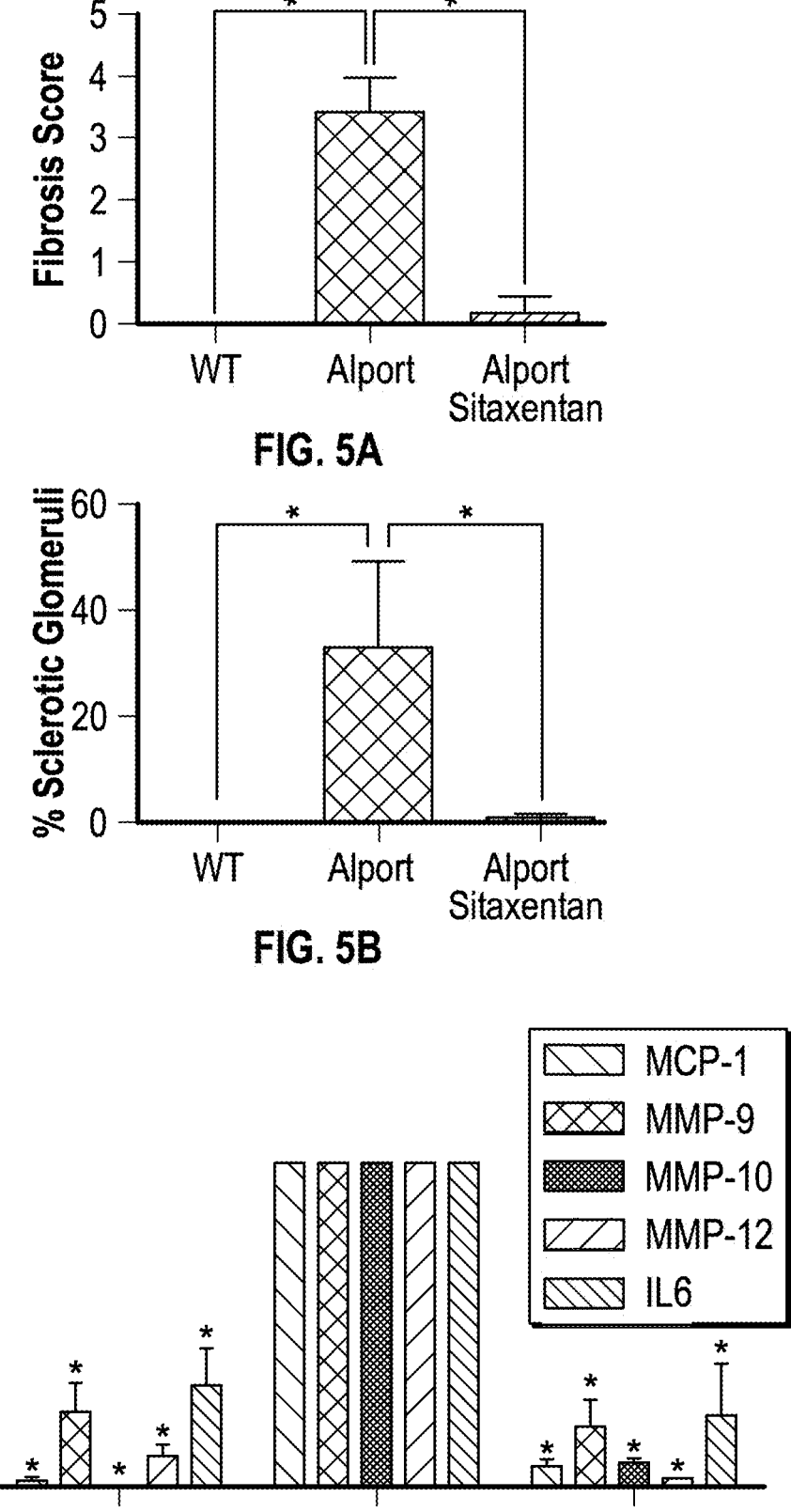
FIGS. 5A to 5C. Sitaxentan treatment ameliorates renal disease in Alport mice.

Endothelin A receptors are expressed primarily on mesangial cells as evidenced by their co-localization with the mesangial cell marker integrin α8 (Dufek et al., 2016, *Kidney Int;* 90(2):300-310). When 129 Sv/J autosomal Alport mice are treated with the small molecule inhibitor for $ET_ARs$, Sitaxentan, GBM laminin α2 deposition is greatly reduced (arrowheads), as is the infiltration of glomerular capillaries with mesangial filopodia (integrin α8 immunopositivity adjacent to laminin α5 immunopositivity, a fully infiltrated capillary is marked with an arrowhead) (FIG. 3A). In addition, the classic GBM dysmorphology associated with Alport syndrome is normalized (FIG. 3B). Treated mice also show significantly delayed onset and reduced progression of proteinuria and BUN (FIG. 4). In addition, fibrosis scores, % glomerulosclerosis, and glomerular mRNA expression of cytokines and metalloproteinases functionally associated with the progression of the glomerular disease are reduced to near control levels in Sitaxentan-treated mice (FIG. 5).

Lifespan in the Sitaxentan-treated mice was only increased by 20%, however the glomeruli and the interstitium of the treated mice continued to show attenuated disease even near end stage. This marginal improvement in lifespan is likely due to the toxic off target effects of the drug (FIG. 1). At a higher dose (30 mg/kg once daily) the Alport mice actually had a shorter lifespan than vehicle treated Alport mice, consistent with this notion. The basic structure of the analysis to be performed in Aim 1 is as outlined above for the small molecule inhibitor studies. It is important to note that changes in blood pressure were not observed in mice treated with Sitaxentan, since it is established that endothelial cell-specific EDN1 knockout mice have low blood pressure (Kisanuki et al., 2010, *Hypertension;* 56(1): 121-8).

Currently there are no available anti-ET-1 antibodies with function neutralizing capacity. This is likely because the properly folded 21 amino acid biologically active peptide contains two disulfide bonds. Producing the immunogen required that an additional C-terminal cysteine be added for conjugation to KLH. If the peptide is already folded, the C-terminal cysteine cannot be added. A scheme was devised to properly fold the peptide during synthesis while bound to KLH. Cleaving the bound ET-1 followed by mass spectroscopy analysis showed that under these conditions 80% of the peptide is properly folded.

Figure 6:
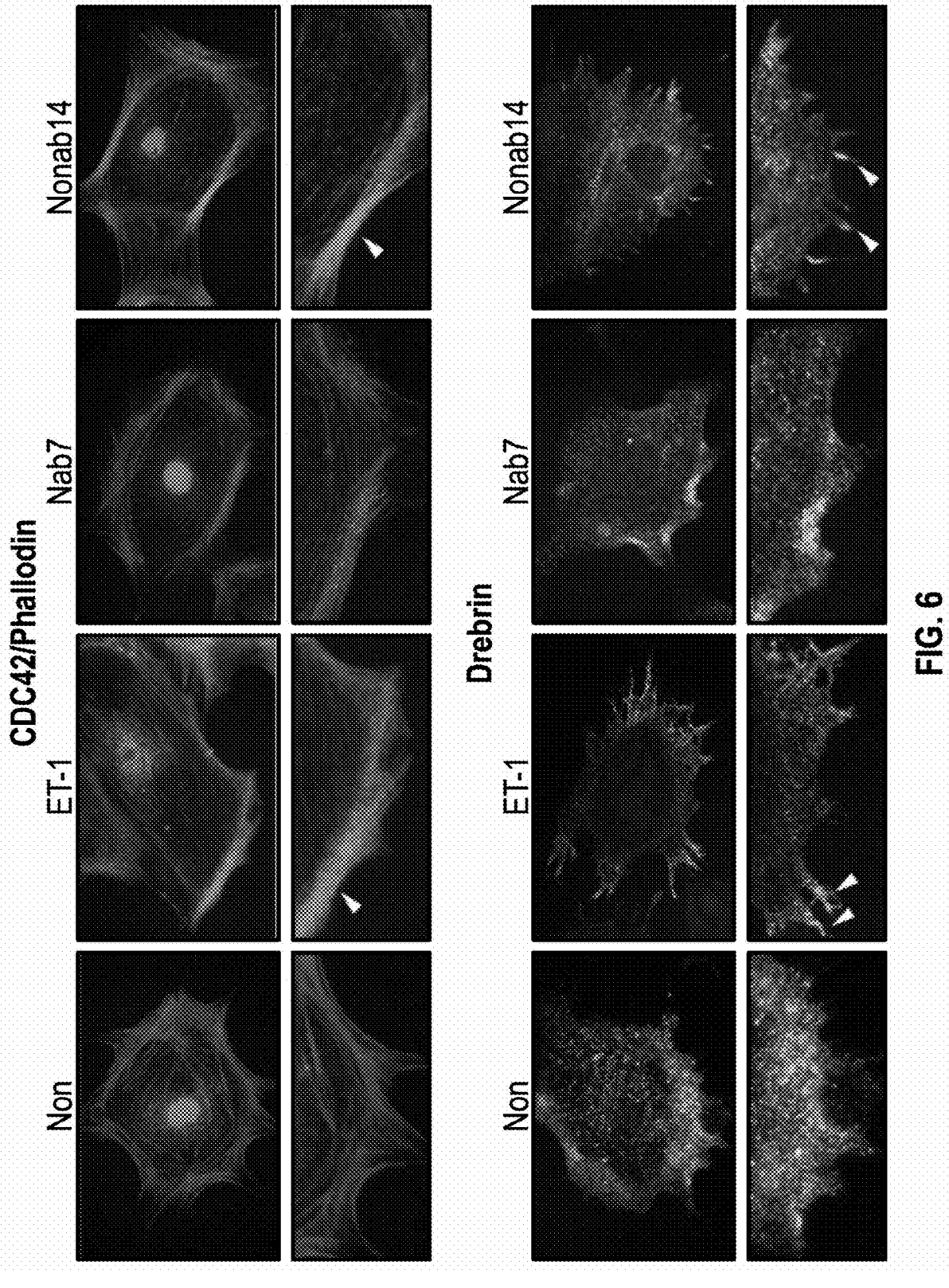
FIG. 6. Demonstration of function neutralization of ET-1 activation in cultures mesangial cells. Upper panels show that ET-1 activation (ET-1) causes loss of actin stress fibers (red) and migration of CDC42 (green) to the plasma membrane (arrowheads). Lower panels show that ET-1 activation also results in the formation of drebrin-positive actin microspikes, which are newly formed filopodia (arrowheads). Pretreatment of cells with neutralizing antibody Nab7 prevents both CDC42 activation and the formation of drebrin-positive actin microspikes, while pre-treatment of ET-1 reactive antibodies that lack function neutralizing activity (Nonab 14) does not. Non-untreated cells.
Figure 7:
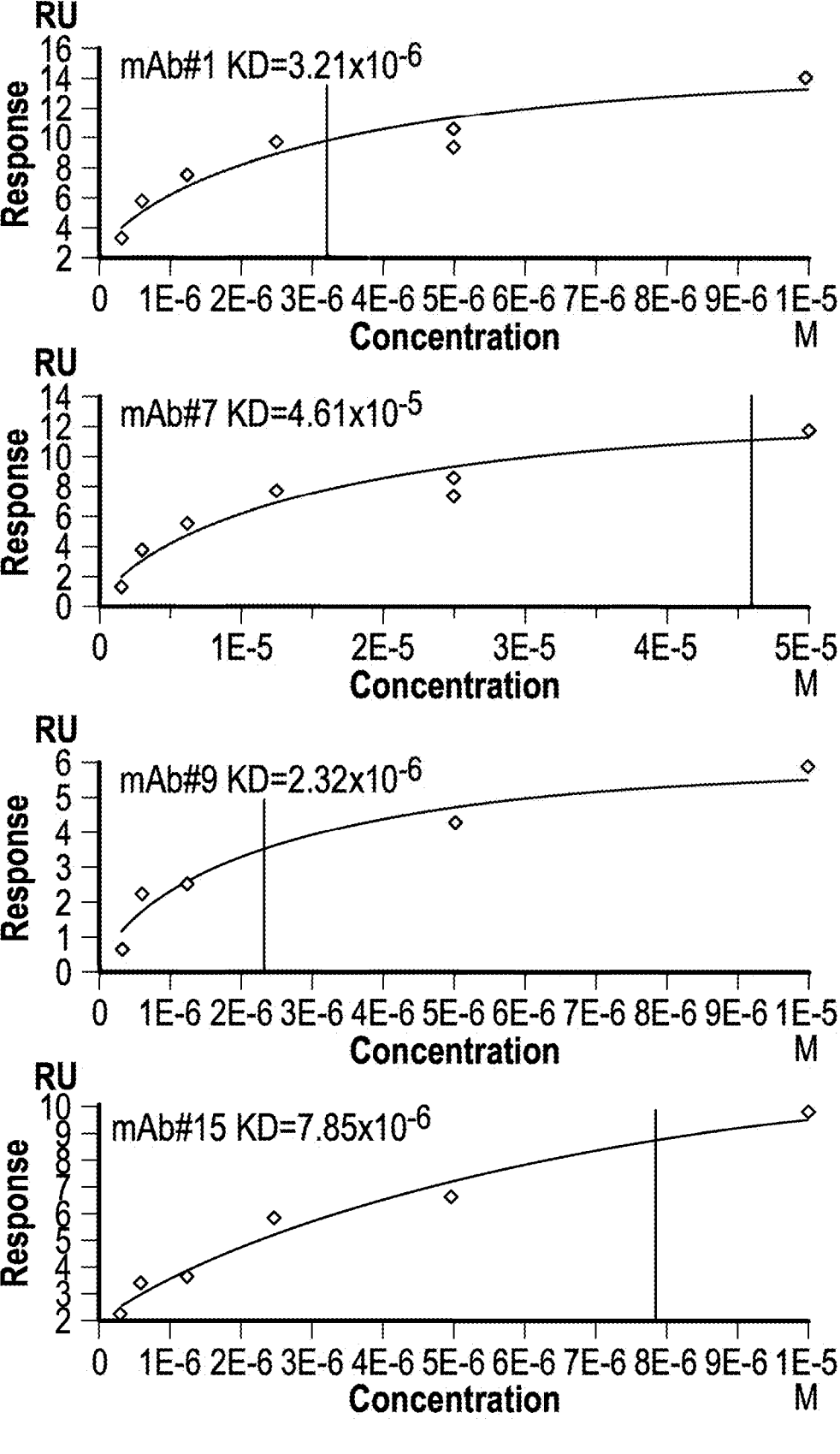
FIG. 7. Four candidate ET-1 neutralizing antibodies were analyzed for relative affinity via Biacore analysis. The antibody was immobilized, and active ET-1 was used as the analyte. The analysis indicates that all of the antibodies are of relatively low (micromolar) affinities. This is not unexpected given that the immunogen (ET-1) is a tiny globular peptide.

Short globular peptides with multiple disulfide bonds make poor immunogens, requiring several more boosts than normally needed to generate high titers. When necessary titers were available, hybridoma screening identified four function neutralizing antibodies (screened in the mesangial cell-based bioassay, see FIG. 6) out of 20 that reacted to biologically active ET-1 by ELISA. Between 25 and 40 milligrams of affinity purified mAbs for all four positive clones were used to re-validated function neutralizing activity in the bioassay. The antibodies were graded for relative affinity using Biacore surface plasmon resonance assay. The results in FIG. 7 show that all four of the antibodies have affinities in the micromolar range, which is low, but expectedly low given the nature of the immunogen. This is expected to improve upon affinity maturation.

Figure 8:
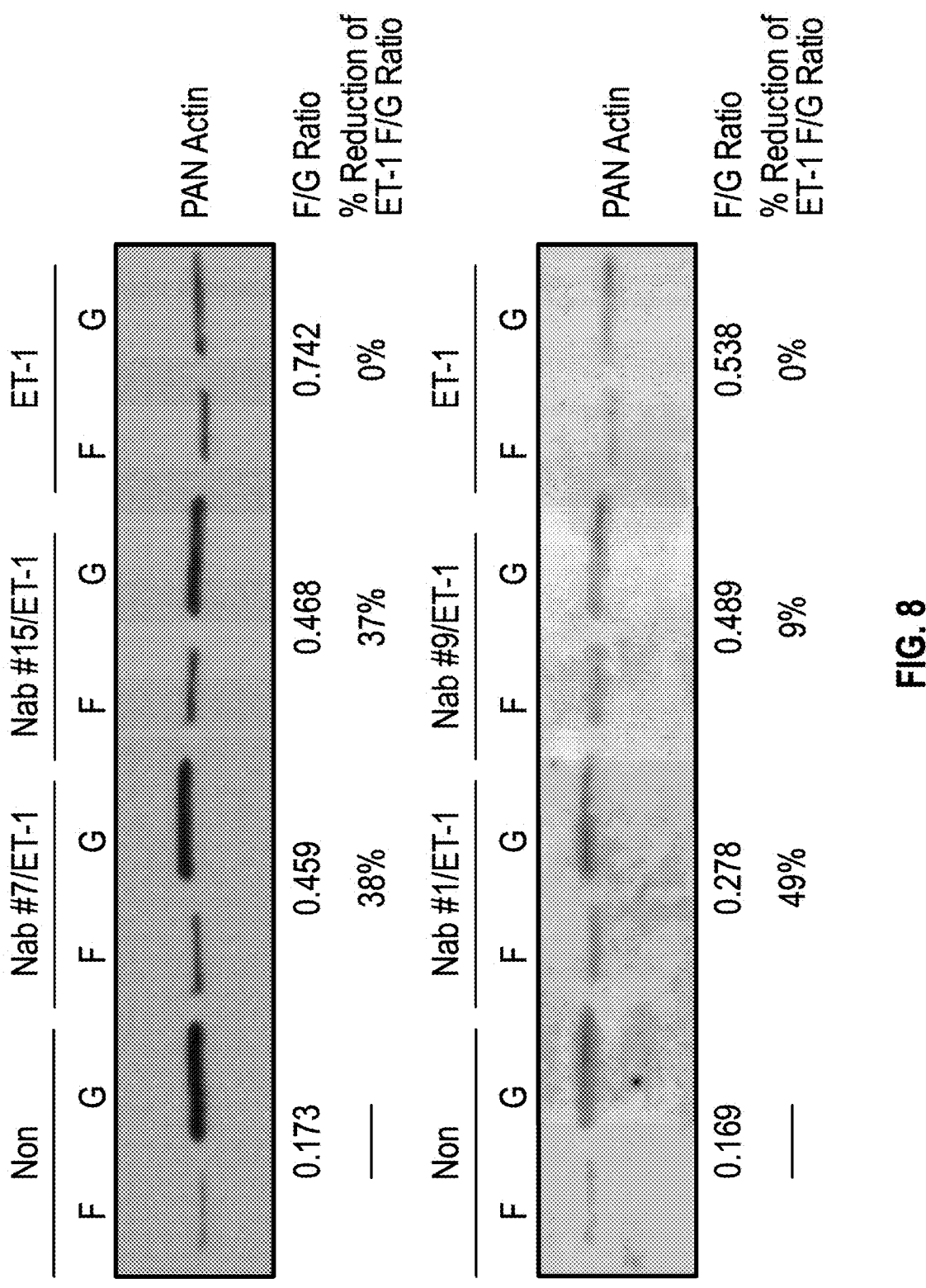
FIG. 8. Measurement of the ratio of F-actin (polymer) to G-actin (monomer) is a useful method of examining experimental changes in actin polymerization. Equal amounts of mesangial cell lysates were subjected to differential centrifugation to separate filamentous actin (F-actin) from globular actin (G-actin) and Pan Actin immunoblots were performed from each sample. The corresponding band was quantified and expressed as the ratio F-actin/G-actin (F/G Ratio). ET-1 treatment results in an increase of actin polymerization. Treatment with the function neutralizing antibodies results in a reduction in the degree of actin polymerization by ET-1. The % Reduction of ET-1 F/G Ratio in thus a relative measure of the neutralizing capacity for each function-neutralizing antibody, allowing them to be ranked.

To rank the antibodies, a biochemical assay for actin polymerization was used. ET-1 treatment of cultured mesangial cells induces the formation of filamentous actin (F-actin), likely accounting for the formation of actin microspikes (FIG. 6). This can be measured by pelleting the F-actin and measuring the ration of F-actin to globular actin (G-actin), the latter, which remains in the supernatant. Inclusion of function neutralizing antibodies prevents the ET-1 induced formation of F-actin. The degree to which F-actin polymerization is inhibited (% reduction of ET-1 F/G ratio) is thus relative to the efficacy of the function neutralizing capacity of the antibody, allowing the four antibodies to be ranked (FIG. 8).

Even though Antibody #7 (Aby #7) had lower affinity than the other antibodies, it showed very promising pharmacodynamic properties in vivo, and good function neutralizing activity in the biochemical assay thus was viewed as a promising candidate. Antibody #15 (Aby #15) did not perform as well as Ab #7 in vivo, however Antibody #1 (Aby #1) looked promising in the mouse model. Based on this data, Aby #1 and Aby #7 were chosen for further development. Aby #15, which has also been deposited with the ATCC, will not be further developed unless the other two antibodies (Aby #1 and Aby #7) do not perform up to standards.

Figures 9A, 9B, 9C:
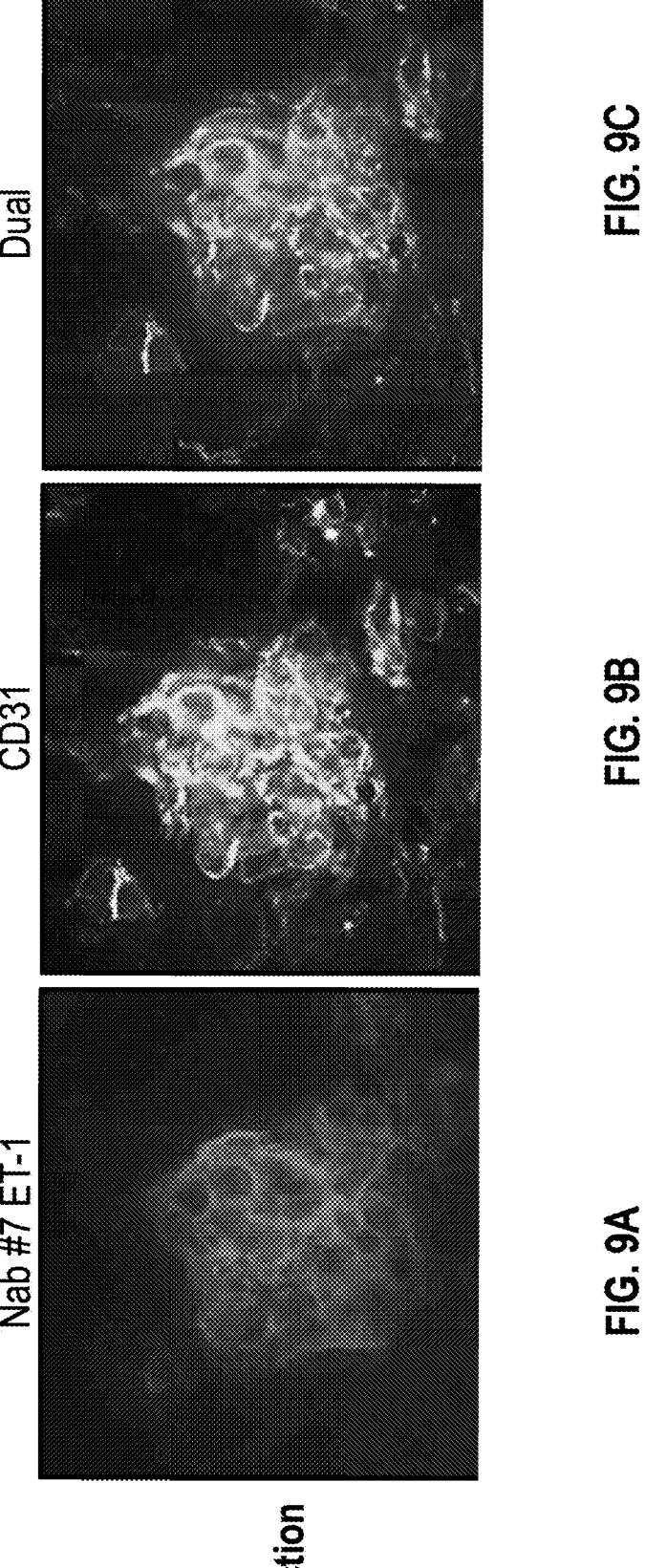
FIGS. 9A to 9C. Cryosections from wild type mouse kidney were dual-stained with labeled mAb #7 and antiCD31 antibodies.

It has been previously shown that active ET-1 localizes to the glomerular endothelium ((Dufek et al., 2016, *Kidney Int;* 90(2):300-310). To see if the present neutralizing antibodies show appropriate localization, antibodies were labelled with phycoerythin and dual localization performed with the endothelial cell marker, anti-CD31. FIG. 9 shows that Aby #7 does indeed react with endogenous ET-1 in the endothelium. To demonstrate that injected neutralizing antibodies will target the glomerular endothelium, 20 micrograms of the labeled antibodies were injected subcutaneously. After 3 hours the animals were transcardially perfused with PBS and kidneys cryosectioned and immediately examined using a fluorescence microscope. The results in FIG. 10 illustrate correct targeting of the antibodies to the glomerular endothelium. Similar results were obtained with Aby #1.

Experimental Design:

PK and PD analysis. For both 129 Sv autosomal Alport model and C57Bl/6 XLAS model PK analysis followed by PD analysis will be assayed. Dose response will be analyzed in vivo. Minimal dose with best PD outcomes chosen for PD studies. Significant improvement in renal function and scoring parameters for both the 129 Sv autosomal Alport model and the Bl/6 XLAS model is expected. If either antibody does not show significant improvement of renal disease at optimum doses, it will not advance for affinity maturation. It is notable that Aby #7 has already achieved or is approaching significance for a number of these parameters (FIGS. 11, 12, and 13).

Affinity Maturation. Affinity maturation for antibodies #1 and/or #7 will be performed by a commercial partner (Creative Biolabs, Inc.). Significant improvement in affinity will be followed by re-testing for PD parameters in both models. After significant improvement in affinity, antibodies will advance to lifespan studies.

Lifespan Studies. Lifespan studies plus/minus ramipril (using optimal dose of mAbs following affinity maturation) at both early and late interventions for both autosomal and X-linked Alport mouse models.

Humanization. Humanization of antibodies will be done, followed by retesting of PD efficacy to assure function neutralizing capacity has been maintained.

For all studies both male and female mice will be used, as statistically significant differences have not been observed between the two sexes.

Specific Aim 1

It is expected that the two mAbs (Ab #1 and Ab #7) chosen for further development will demonstrate significant pharmacodynamic efficacy and that affinity maturation will improve the pharmacodynamic efficacy to levels observed for $ET_AR$ receptor inhibitors.

Pharmacokinetics: The two antibodies are IgG1kappa. Mouse monoclonal antibodies tend to have a half-life in mice of approximately 8 days (Covell et al., 1986, *Cancer Res;* 46(8):3969-78). The half-life can vary by specific properties of the antibody itself and by dose, with lower doses showing reduced half-lives relative to higher doses (Marathe et al., 2012, *Pharm Res;* 29(11):3180-7). Doses of 10, 20, and 30 mg/kg will be tested for the two antibodies using 3 animals per concentration in 6-week-old 129 Sv mice and 10-week-old C57 Bl/6 mice. Following subcutaneous injection of antibody, blood will be collected at 2, 4, 8, and 16 days, and the plasma assayed for anti-ET-1 antibodies by ELISA. The doses were chosen based on preliminary studies for mAb #7. An ELISA assay for anti-ET-1 antibodies utilizing immobilization of full-length mouse ET-1 (Biosource) will be used. Only antibodies that react with the endothelin protein will bind. Non-reactive antibodies will be washed away. Dilutions of the purified antibodies will be used as positive controls and non-reactive IgG as negative controls.

Antibody #7 has already been tested for PK using a 20 mg/kg dose injected subcutaneously. The results demonstrate a half-life of 6.5 days-within expected range for a mouse mAb.

Blood pressure measurements. It is known that endothelial cell-specific EDN1 knockout mice have reduced blood pressure relative to age/strain-matched wild type mice (Kisanuki et al., 2010, *Hypertension;* 56(1):121-8). It is possible therefore that high doses of the ET-1 function neutralizing antibodies might result in reduced blood pressure. As previously shown, elevated blood pressure results in accelerated disease expression in the Alport mouse (Meehan et al., 2009, *Kidney Int;* 76:968-976) and thus reduced blood pressure could contribute to renoprotection in a way that does not synergize with ACE inhibitor therapy. Blood pressure will be measured in wild type and Alport mice at the optimal dose of mAbs. Five animals per group (vehicle versus mAb-treated) will be tested for blood pressure every other day from 5 to 6 weeks of age (3 weeks following the initial dose, which is administered at 2 weeks of age). If significantly reduced blood pressure is detected (using the CODA tail cuff system, Kent Scientific) this will be considered when interpreting the lifespan data for dual therapy in Aim 3. It is notable that Sitaxentan had no effect on blood pressure in the 129 Sv autosomal Alport mouse model ((Dufek et al., 2016, *Kidney Int;* 90(2):300-310).

Pharmacodynamics. The 129 Sv Alport mouse model and the C57Bl/6 XLAS model are both are very reliable models with regard to the kinetics of renal and glomerular disease development and are used all over the world. The assays used in an analysis of the function neutralizing anti-ET1 antibodies have been applied in numerous published works (Zallocchi et al., 2013, *Am J Pathol;* 183(4):1269-80; Delimont et al., *PLoS One,* 2014 Jun. 10; 9(6); and Dufek et al., 2016, *Kidney Int;* 90(2):300-310), as well as a large number of sponsored research initiatives performed under contract with biotechnology companies interested in developing drugs that ameliorate Alport renal disease in the mouse model. Based on these studies and the power analyses provided below, the number of animals used in each cohort will be sufficient to provide statistically significant changes in these measures at the pre-determined thresholds.

For each antibody, mice will be treated twice weekly (more often if PK shows shorter half-lives than expected) at doses of 10, 20, and 30 mg/kg by sub-cutaneous injection. These will be scored for glomerulosclerosis and fibrosis and assayed for proteinuria and BUN. The optimal dose will be chosen for an expanded PD analysis. Based on power analysis (FIG. 16 and FIG. 17), 10 Alport mice will be treated per cohort for both the C57 Bl/6 XLAS model and the 129 Sv autosomal Alport model. Cohorts will be Alport vehicle; Alport nAb; wild type vehicle; wild type nAb. The 129 Sv model will be treated from 3 to 7 weeks of age, and the C57 Bl/6 will be treated from 5 to 15 weeks of age. Urine will be collected weekly for the autosomal model and biweekly for the XLAS model. Urine will be screened for ET-1 (by ELISA to look for clearance of the cytokine) and for albuminuria (by ELISA). Blood will be collected at the time of tissue harvest for BUN measures.

Figure 2:
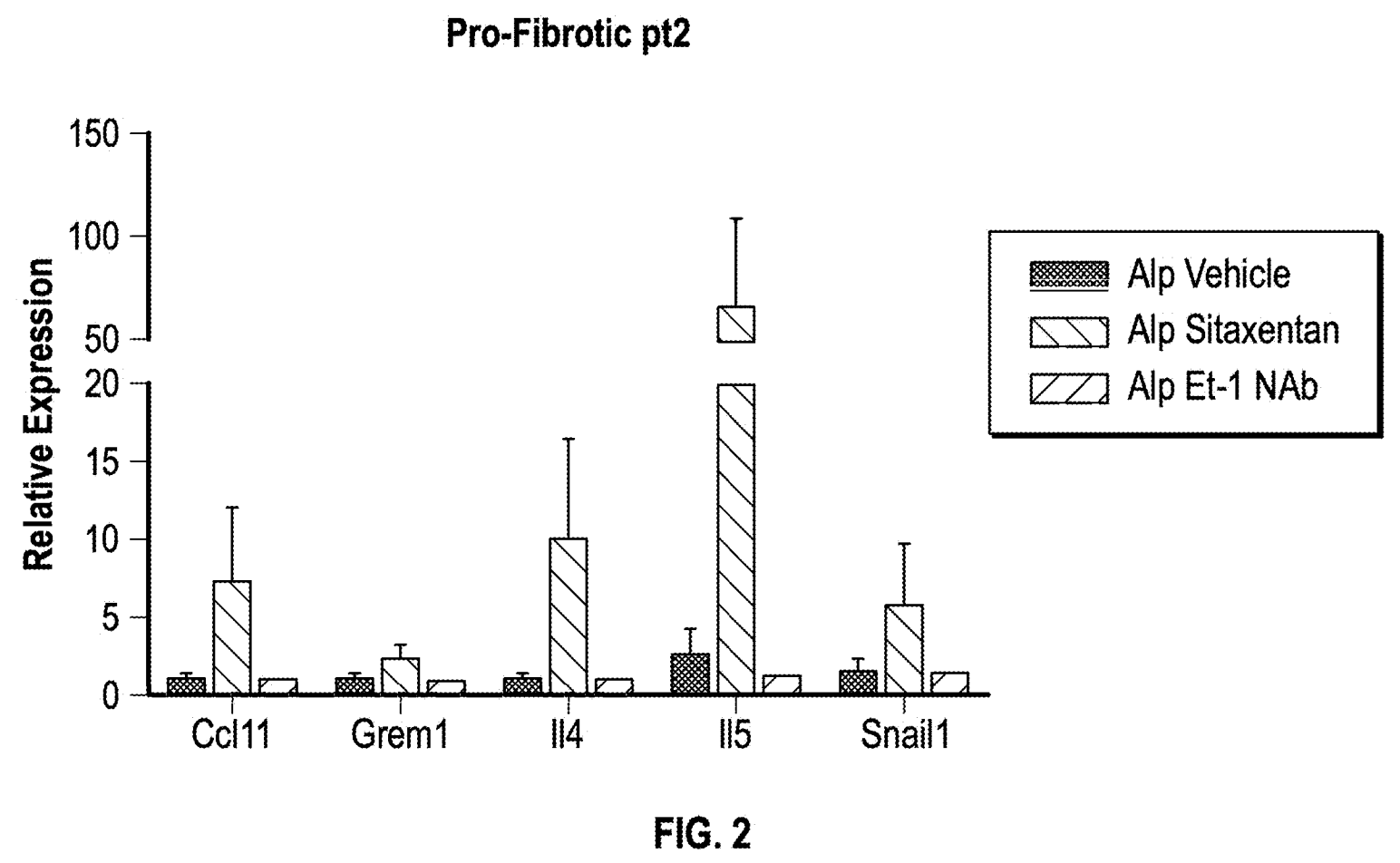

At harvest, mice will be perfused transcardially with PBS, and one kidney clamped at the renal artery and the other perfused with Dynabeads for magnetic isolation of glomeruli. The other kidney will be halved, and a small sample of renal cortex fixed for transmission electron microscopic (TEM) analysis and a second sample of renal cortex used for RNA isolation. The other half of the bisected kidney will be embedded in OCT for immunohistochemical analysis. RNA from glomeruli (autosomal model) will be analyzed by real time RT-PCR for MMP-10, MMP-12, IL6, and MCP-1. For the XLAS model, glomerular RNA will be analyzed for MMP-9, -10, -12, and -14. RNA from renal cortex (both models) will be analyzed by real time RT-PCR for TNF-alpha, CTGF, MMP-2, and MMP-9. These transcripts are chosen because they are significantly up-regulated in 7 week 129 Sv autosomal Alport mice and have served as reliable markers for therapeutic approaches aimed at ameliorating glomerular disease/interstitial fibrosis in the model (Dufek et al., 2016, *Kidney Int;* 90(2):300-310). Power analysis for the XLAS glomerular RNA shows we should see statistically significant changes in the MMPs chosen if as an indication of PD efficacy. Cortical RNA from the XLAS model has not been previously analyzed. To assure PD efficacy, glomerular and cortical RNAs will be pooled from 3 samples each into 3 groups and analyze using the mouse fibrosis microarray template (QIAGEN). This template, which measures 84 genes associated with fibrosis, has been found to be very informative (FIG. 2). Immunohistochemical analysis will include antibodies for collagen 1, CD45 (pan leukocyte), fibronectin, smooth muscle actin (to detect interstitial myofibroblasts), WT-1 (to score podocyte numbers), and integrin alpha 8/laminin $\alpha$5 (to examine filopodial invasion of glomerular capillaries). Collagen 1 and CD45 staining will be blindly analyzed for fibrosis scoring, and fibronectin staining will be blindly analyzed for glomerulosclerosis scoring. Transmission electron microscopy (TEM) will be performed on five mice from the dosing group showing the best renoprotection based on our analyses to examine the GBM architecture. All immunohistochemical analysis will be imaged using confocal microscopy. For all studies albuminuria (normalized to urinary creatinine) will be assessed weekly (for autosomal model) or biweekly (for XLAS model) and BUN (normalized to serum creatinine) at the time of tissue harvest.

If significant improvement is observed, the hybridomas will be sent to Creative Biolabs for affinity maturation. If antibody #1 performs as well or better than antibody #7, it will be chosen because it has a higher affinity to start with.

The affinity mature murine antibodies will be re-tested in one or both animal models as above, and the optimal dose used in the lifespan studies (Aim 2).

One of the neutralizing antibodies (mAb #7) has been tested at several concentrations. The results in FIG. 11 show that treatment using the 20 mg/kg dose twice weekly significantly reduced fibrosis and glomerulosclerosis. FIG. 12 demonstrates that expression of genes associated with glomerular and interstitial disease progression show mixed results. IL-6 and MCP-1 were significantly reduced in the glomerulus, while MMP-9 and TNF-α were significantly reduced in the renal cortex. For blood urea nitrogen levels (FIG. 13) the results, while trending towards significance, are not yet significant. The data are encouraging as they demonstrate this antibody has function neutralizing activity in vivo and significantly reduces many of the parameters associated with Alport renal disease. These numbers will likely improve by inclusion of additional mice.

Ambrisentan will be run alongside of the neutralizing Ab studies for both PD and lifespan (both models). This will be done as a head-to-head comparison with the ET-1 neutralizing antibody approach. Ambrisentan is chosen because it is currently used in humans for the treatment of pulmonary hypertension. Sitaxentan was discontinued due to liver toxicity. administer Ambrisentan will be administered by oral gavage once daily at a dose of 30 mg/kg. The dose was determined as a prelude to these studies in a pharmacodynamic dose response experiment shown in FIG. 14. At 30 mg/kg from 3 to 7 weeks fibrosis was almost completely inhibited, consistent with what that observed for Sitaxentan (Dufek et al., 2016, *Kidney Int;* 90(2):300-310). Ambrisentan will be used to treat mice from 3 to 7 weeks of age.

Analysis will be done as for mice treated with the neutralizing antibodies. These assays are designed to provide definitive data as to whether the antibodies have function neutralizing activity in vivo. Based on the preliminary evidence with Ab #7, the antibodies are indeed functional in vivo even though they are of relatively low affinity. Based on this and with the history of affinity maturation resulting in more effective mAb pharmacodynamic efficacy (Wang et al., 2008), it is expected that affinity maturation will indeed improve antibody performance in the Alport models. It is possible that the nAbs in their current state may not outperform Ambrisentan with regard to the measures of renoprotection conducted in PD experiment. However, following affinity maturation, it is expected that the nAbs will perform at least as well as Ambrisentan and possibly better, as the nAbs do not induce expression of the profibrotic cytokines and the snail transcription factor which are induced by Ambrisentan and Sitaxentan in the Alport glomeruli (FIG. 2).

Specific Aim #2

ET-1 neutralizing antibodies will synergize with ramipril therapy, more than doubling the lifespan of 129 Sv autosomal Alport mice. ACE inhibitors are the standard of care for most forms of chronic kidney disease and Alport syndrome is no exception. It was found long ago that ACE inhibition with ramipril therapy doubled the lifespan of 129 Sv autosomal Alport mice if administered before the onset of proteinuria (Gross et al., 2003, *Kidney Int;* 63(2):438-46). The benefit of ACE inhibition in humans with Alport syndrome also shows a significant reduction in proteinuria and a significant increase in lifespan in an ongoing study (Gross et al., 2012, *Kidney Int;* 81(5):494-501). Like the mouse studies, humans that start ACE inhibitor therapy early show greater benefit than those who start after the renal disease is established. Thus, ACE inhibition is now established as the current standard of care for Alport patients. Any novel therapeutic approach would be employed in combination with ACE inhibitors, and thus must provide additive/synergistic benefit in controlling renal disease progression. So far, no therapeutic approach has been identified that has these characteristics.

Predictors that antibody treatment will synergize with ramipril are the fact that ramipril therapy reduces blood pressure (which reduces biomechanical strain) while Sitaxentan treatment does not. Earlier work showed that biomechanical strain plays an important role in accelerating the progression of Alport glomerular/renal disease (Meehan et al., 2009, *Kidney Int;* 76:968-976). Hypertensive (L-NAME salt-treated) Alport mice showed significantly faster progression than normotensive (untreated) Alport mice. A second predictor is that ramipril-treated mice showed a degree of GBM damage that was comparable to untreated Alport mice (Gross et al., 2003, *Kidney Int;* 63(2):438-46) while Sitaxentan-treated mice showed significantly reduced GBM damage compared to vehicle-treated Alport mice (Dufek et al., 2016, *Kidney Int;* 90(2):300-310).

Life span studies. The two best antibodies will be tested at their optimum concentrations based on Specific Aim 1, either alone or in combination with Ramipril (10 mg/kg in the drinking water). Dosage of ramipril was determined by measuring the daily intake of water at the various ages for both males and females. This intake was used to calculate the concentration of ramipril in the water, which is replaced every four days. This approach has been used to test ramipril therapy, reproducing the results of Gross et al. (2003). Cohorts will be: 10 Alport mice vehicle treated; 10 Alport mice each given either of the neutralizing antibodies, 10 Alport mice ramipril treated, and 10 mice given both ramipril and either of the neutralizing antibodies. End point is when animals lose greater than 15% of their peak body weight. This generally occurs within 3-5 days of death and avoids severe wasting and maintains compliance with IACUC recommendations.

Data will be plotted as percent survival. The number of mice used is based on the number needed to provide the statistical power to identify >20% increase in lifespan over vehicle based on previous results (FIG. 16). Antibodies that improve lifespan significantly over Ramipril alone will be candidates for humanization. This will again be done under contract with Creative Biolabs. Humanized antibodies will be retested in both models (short-term study as in Aim 1) to assure retention of function neutralizing activity.

Lifespan studies are straightforward. The number of animals per group, based on power analysis (FIGS. 16 and 17), assures that an increase in lifespan the data will be statistically significant. Based on previous work with $ET_AR$ inhibitors (demonstrating a 20% increase in lifespan, even though the drug is renotoxic (FIG. 1, FIG. 2, and Dufek et al., 2016, *Kidney Int;* 90(2):300-310)), a significant increase in lifespan is expected with function neutralizing antibodies for ET-1. A greater increase compared to $ET_AR$ inhibition is expected, given the lower toxicity the biologics compared to the small molecules (FIG. 2). This might be true even before affinity maturation. Furthermore, due to the long half-life and excellent bioavailability of antibodies, there will be no troughs in the drug levels, which should improve outcomes over Sitaxentan and Ambrisentan, which has a half-life of 6 hours in mice, and are given once daily. This short half-life results in peaks and troughs, which can result in poorer coverage than what is possible with antibody therapies. It is expected that nAb therapy will be at least additive with Ramipril. In Ramipril-treated animals with established proteinuria it is harder to predict the results, however if it is indeed significantly more beneficial than Ramipril alone, it would be the first drug in its class to perform in this manner, and likely fast-tracked to human clinical trials. Using the affinity optimized antibodies will provide a stringent test as to whether ET-1 blockade in combination with ACE inhibition is indeed a superior therapeutic approach compared to those tested to date. Success in mice will pave the way for testing the efficacy of ET-1 blockade in concert with Ramipril (or ARB) therapy in Alport patients.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

5. The antibody or antigen binding fragment thereof of claim 4, comprising an Fc region comprising tyrosine (Y) at amino acid position 252, threonine (T) at amino acid position 254, and glutamic acid (E) at amino acid position 256, wherein the numbering corresponds to the EU index in Kabat.

6. The antibody or antigen binding fragment thereof of claim 1, wherein the antibody neutralizes the activity of human endothelin-1.

7. A composition comprising the antibody or antigen binding fragment thereof of claim 1.

8. A method of treating Alport syndrome in a subject, the method comprising administering an effective amount of an antibody or antigen binding fragment thereof of claim 1 to the subject.

9. A method of preventing glomerular disease progression in a subject diagnosed with Alport syndrome, the method comprising administering an effective amount of an antibody or antigen binding fragment thereof of claim 1 to the subject.

10. A method of treating glomerulonephritis in a subject, the method comprising administering an effective amount of an antibody or antigen binding fragment thereof of claim 1 to the subject.

11. A method of inhibiting Alport glomerular pathogenesis in a subject; the method comprising:

---

---

What is claimed is:

1. An antibody or antigen binding fragment thereof capable of specifically binding human endothelin-1, the antibody or antigen binding fragment thereof comprising a heavy chain variable region complementarity determining region (CDR) 1, a heavy chain variable region CDR2, a heavy chain variable region CDR3, a light chain variable region CDR1, a light chain variable region CDR2, and a light chain variable region CDR3 of the monoclonal antibody produced by the hybridoma cell line Nab #7 3G 9A4 deposited under ATCC Patent Deposit Designation PTA-125818.

2. The antigen binding fragment thereof of claim 1, wherein the antigen binding fragment thereof is selected from the group consisting of a Fab fragment, a Fab' fragment, a F(ab)$_2$ fragment, a Fv fragment, and a single chain variable fragment (scFv).

3. The antibody or antigen binding fragment thereof of claim 2, wherein the antibody or a functional part thereof is fully human, humanized, or chimeric.

4. The antibody or antigen binding fragment thereof of claim 3, comprising a human IgG1 isotype.

determining that the subject is at risk for developing Alport glomerular disease; and administering an effective amount of an antibody or antigen binding fragment thereof of claim 1 to the subject.

12. The method of claim 11, wherein the determination that the subject is at risk for developing Alport glomerular disease is determined by family medical history, genetic testing, immunodiagnostic skin biopsy testing, and/or molecular diagnostic marker testing.

13. The method of claim 12, wherein one or more sensory and/or hearing losses associated with Alport syndrome is treated or prevented.

14. The method of claim 11, further comprising administering an angiotensin-converting enzyme (ACE) inhibitor.

15. The method of claim 14, wherein the ACE inhibitor is selected from ramipril and/or analapril.

16. The method of claim 15, further comprising administering an endothelin receptor antagonist.

17. The method of claim 16, wherein the endothelin receptor antagonist is selected from bosentan, sitaxsentan, ambrisentan, macitentan, sparsentan, and/or altrasentan.

18. A method of treating pulmonary hypertension in a subject, the method comprising administering an effective amount of an antibody or antigen binding fragment thereof of claim 1 to the subject.

19. A method of treating a kidney disease associated with endothelin-1 induced pathogenesis in a subject, the method comprising administering an effective amount of an antibody or antigen binding fragment thereof of claim 1 to the subject.

20. A method of treating diabetic kidney nephropathy in a subject, the method comprising administering an effective amount of an antibody or antigen binding fragment thereof of claim 1 to the subject.

21. A method of inhibiting endothelin-1 induced pathogenesis in a subject, the method comprising administering an effective amount of an antibody or antigen binding fragment thereof of claim 1 to the subject.

22. An antibody or antigen binding fragment thereof capable of specifically binding human endothelin-1, the antibody or antigen binding fragment thereof comprising the heavy chain variable region (VH) and light chain variable region (VL) of the monoclonal antibody produced by the hybridoma cell line Nab #7 3G 9A4 deposited under ATCC Patent Deposit Designation PTA-125818.

23. The monoclonal antibody produced by hybridoma cell line Nab #7 3G 9A4 deposited under ATCC Patent Deposit Designation PTA-125818, or an antigen binding fragment thereof.

* * * * *